US011814200B2

(12) United States Patent
Seal et al.

(10) Patent No.: US 11,814,200 B2
(45) Date of Patent: Nov. 14, 2023

(54) FLUID DISTRIBUTION SYSTEM WITH SINGLE USE MANIFOLD ASSEMBLY FOR SCALED FILLING

(71) Applicant: Cytiva US LLC, Marlborough, MA (US)

(72) Inventors: Michael B. Seal, Hampshire (GB); Bojan Isailovic, Hampshire (GB); Robert Flisar, Dreieich (DE); Jeremy Rautenbach, Cheltenham (AU)

(73) Assignee: Cytiva US LLC, Marlborough, MA (US)

( * ) Notice: Subject to any disclaimer, the term of this patent is extended or adjusted under 35 U.S.C. 154(b) by 0 days.

(21) Appl. No.: 17/934,962

(22) Filed: Sep. 23, 2022

(65) Prior Publication Data

US 2023/0211905 A1 Jul. 6, 2023

Related U.S. Application Data

(60) Provisional application No. 63/295,483, filed on Dec. 30, 2021.

(51) Int. Cl.
*B67C 3/22* (2006.01)
*B65B 3/00* (2006.01)
(Continued)

(52) U.S. Cl.
CPC ............... *B65B 3/003* (2013.01); *B65B 3/12* (2013.01); *B65B 3/34* (2013.01); *B65B 55/24* (2013.01);
(Continued)

(58) Field of Classification Search
CPC .. B65B 3/003; B65B 3/12; B65B 3/34; B65B 55/24; B67C 3/225; B67C 3/007; B67C 3/282; B67C 2003/228
See application file for complete search history.

(56) References Cited

U.S. PATENT DOCUMENTS 2,672,272 A * 3/1954 Harris ..................... B65B 3/003
141/276
5,911,252 A * 6/1999 Cassel ..................... B65B 3/003
604/407
(Continued)

FOREIGN PATENT DOCUMENTS

EP 1525138 A1 4/2005
EP 3845626 A1 7/2021
(Continued)

OTHER PUBLICATIONS

European Patent Office, Extended European Search Report in European Patent Application No. 22216945.0 (dated Jul. 14, 2023).
(Continued)

*Primary Examiner* — Nicolas A Arnett
(74) *Attorney, Agent, or Firm* — Leydig, Voit & Mayer, Ltd.

(57) ABSTRACT

A fluid distribution system includes single use distributor manifolds each having a distributor manifold inlet and a plurality of distributor manifold outlets in fluid communication with the distributor manifold inlet. A set of single use filler manifolds can be sequentially connected to a respective one of the outlets of a single use distributor manifold immediately upstream of the connection point of the set of single use filler manifolds. In embodiments, an upstream distributor manifold can be used to feed fluid to a set of intermediary distributor manifolds where the set of intermediary distributor manifolds corresponds to the number of outlets of the upstream distributor manifold.

20 Claims, 33 Drawing Sheets

(51) Int. Cl.
    *B65B 3/12*           (2006.01)
    *B65B 3/34*           (2006.01)
    *B65B 55/24*          (2006.01)
    *B67C 3/28*           (2006.01)

(52) U.S. Cl.
    CPC .............. *B67C 3/225* (2013.01); *B67C 3/282* (2013.01); *B67C 2003/228* (2013.01)

(56) References Cited

U.S. PATENT DOCUMENTS

| | | | | |
|---|---|---|---|---|
| 6,712,963 | B2* | 3/2004 | Schick | A61M 1/0218 |
| | | | | 210/257.2 |
| 7,343,943 | B2* | 3/2008 | Khan | B65B 3/003 |
| | | | | 141/2 |
| 10,549,248 | B2* | 2/2020 | Brown | A61M 39/223 |
| 10,954,007 | B2* | 3/2021 | Feith | A61J 3/002 |
| 11,319,201 | B2* | 5/2022 | Zumbrum | B67C 3/225 |
| 11,639,240 | B2* | 5/2023 | Goodwin | B65B 1/04 |
| | | | | 53/469 |
| 11,648,182 | B2* | 5/2023 | Oda | A61J 3/002 |
| | | | | 141/27 |
| 2002/0146816 | A1 | 10/2002 | Vellinger et al. | |
| 2013/0220484 | A1 | 8/2013 | De Marco | |
| 2017/0361966 | A1* | 12/2017 | Havel | B65B 39/00 |
| 2021/0139834 | A1 | 5/2021 | Raviv et al. | |
| 2021/0155507 | A1* | 5/2021 | Kamen | C02F 1/441 |
| 2021/0197142 | A1* | 7/2021 | Seal | B01F 23/49 |
| 2021/0197189 | A1* | 7/2021 | Isailovic | G01F 23/268 |
| 2021/0325212 | A1* | 10/2021 | Lamport | B01F 25/4316 |
| 2022/0380069 | A1* | 12/2022 | Cataldo | B65B 59/04 |

FOREIGN PATENT DOCUMENTS

| | | |
|---|---|---|
| EP | 3878612 A1 | 9/2021 |
| JP | 2006-007039 A | 1/2006 |
| RU | 2745125 C1 | 3/2021 |
| WO | WO 2009/100428 A1 | 8/2009 |
| WO | WO 2021/164912 A1 | 8/2021 |

OTHER PUBLICATIONS

Japan Patent Office, Notice of Reasons for Rejection in Japanese Patent Application No. 2022-209815 (dated Aug. 29, 2023).

* cited by examiner

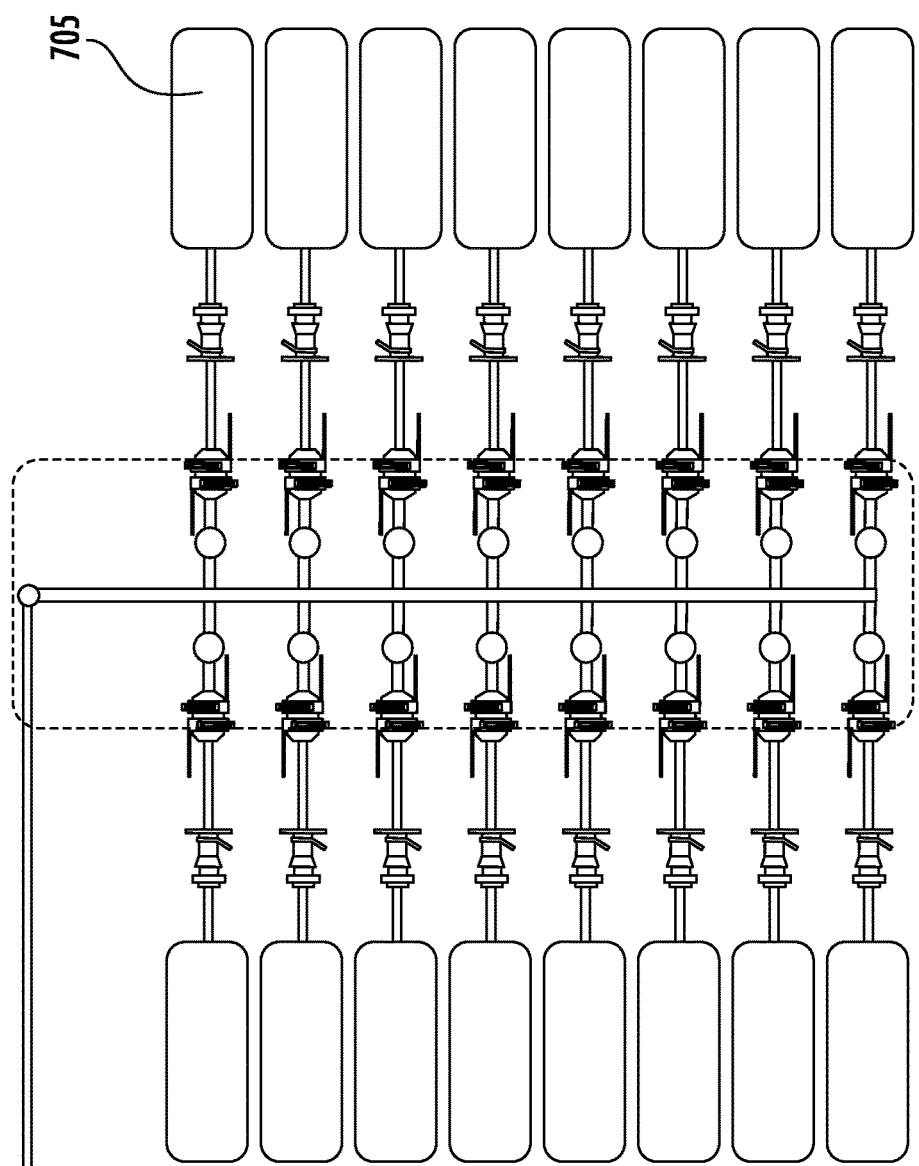
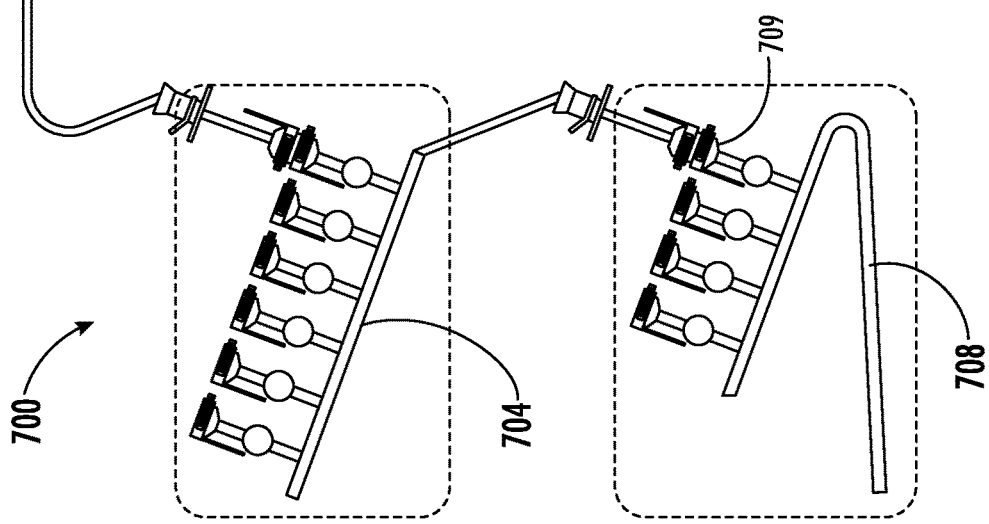
FIG. 14

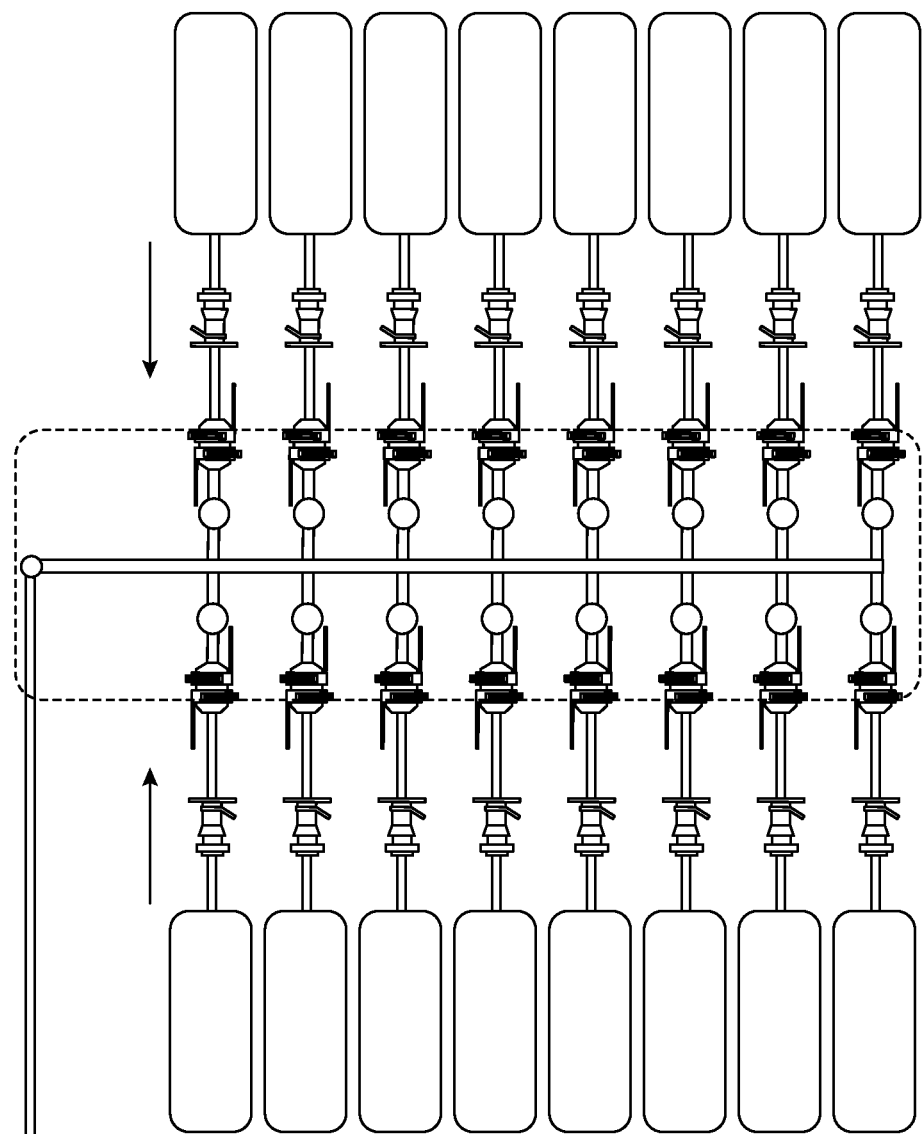
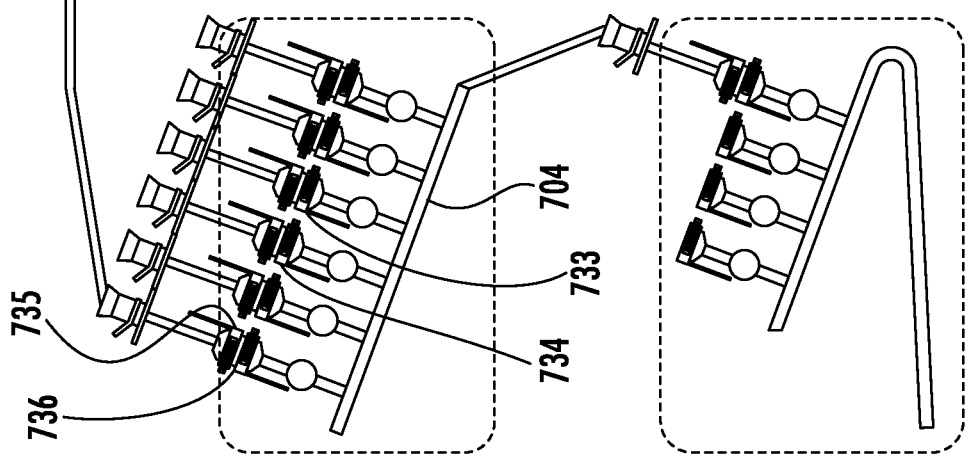
FIG. 23

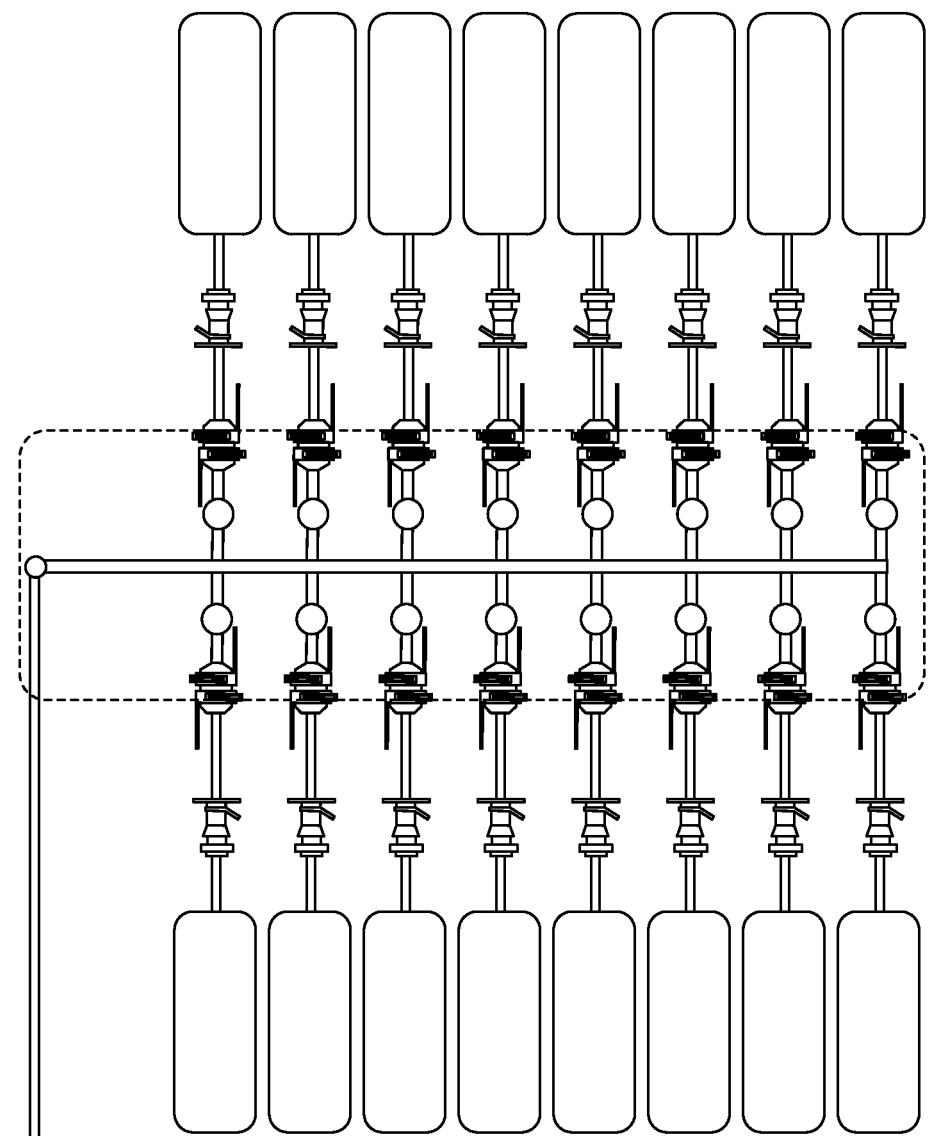
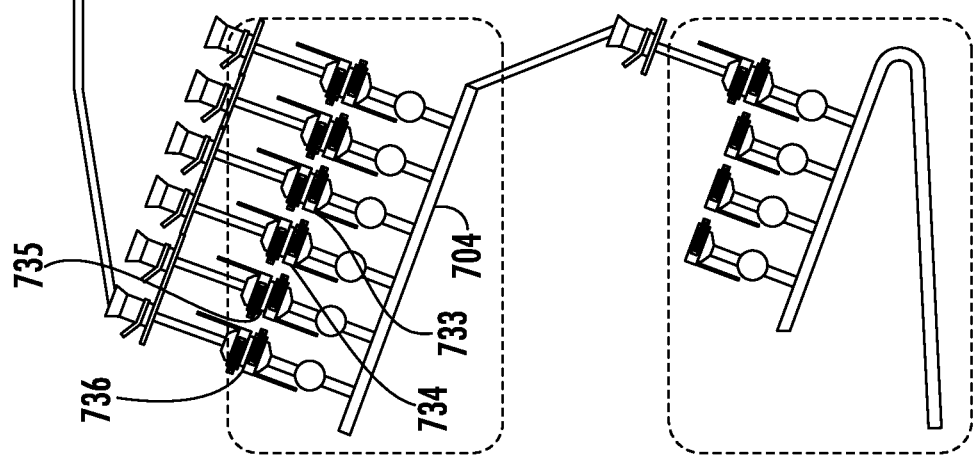
FIG. 24

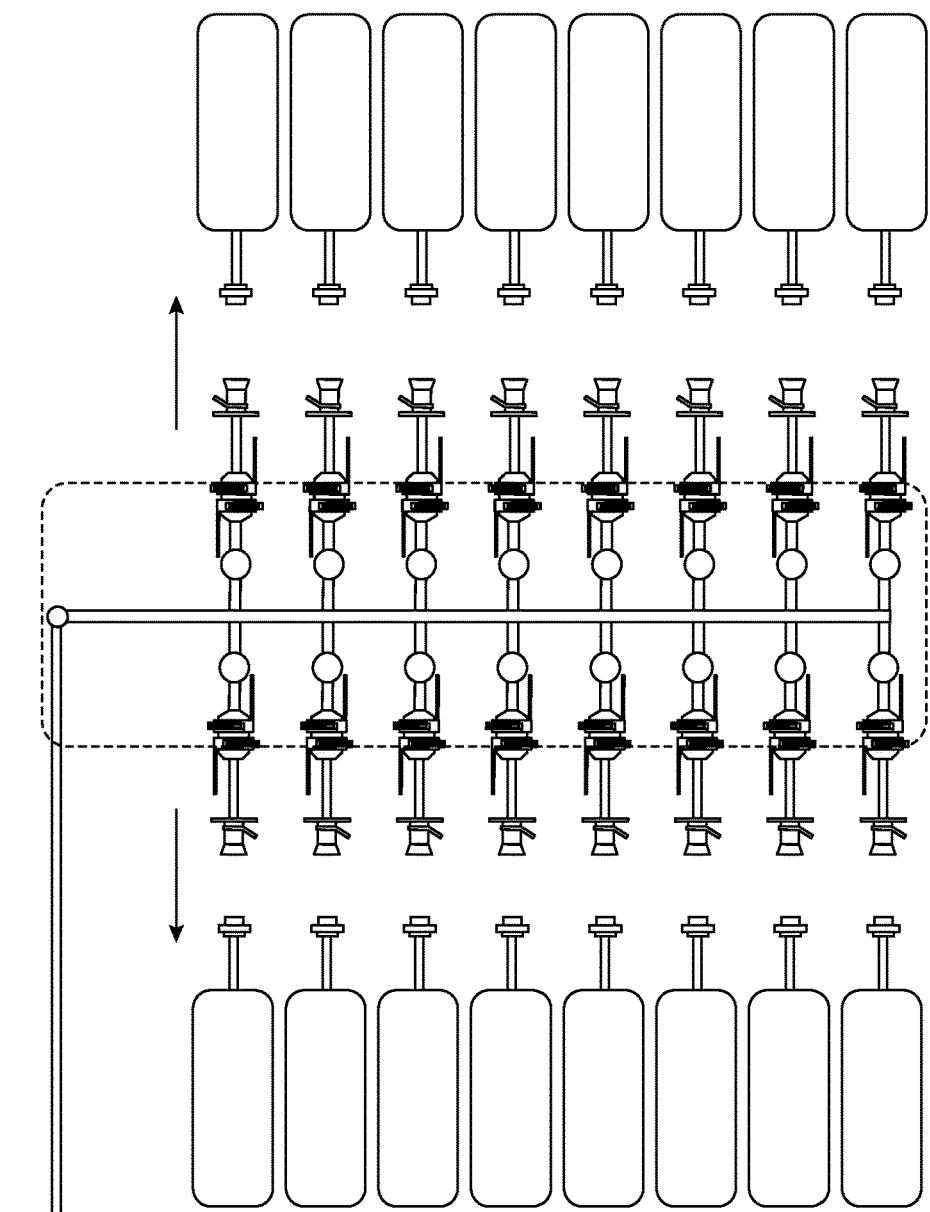
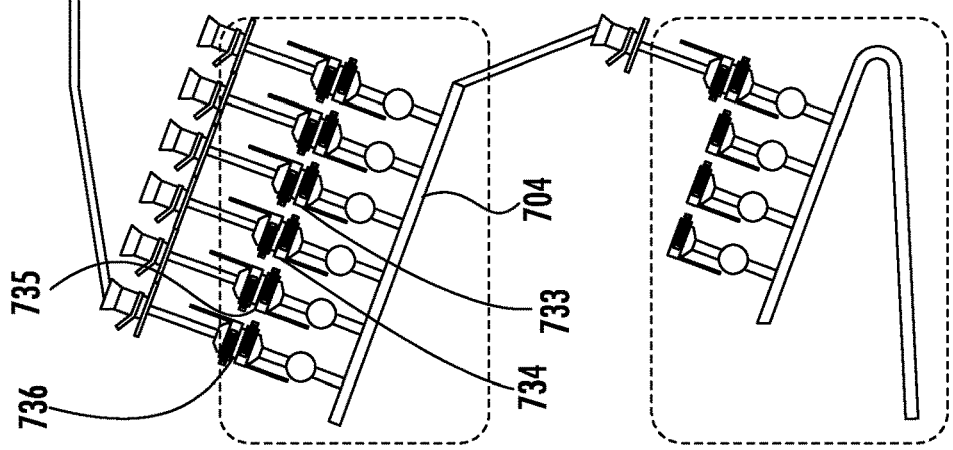
FIG. 25

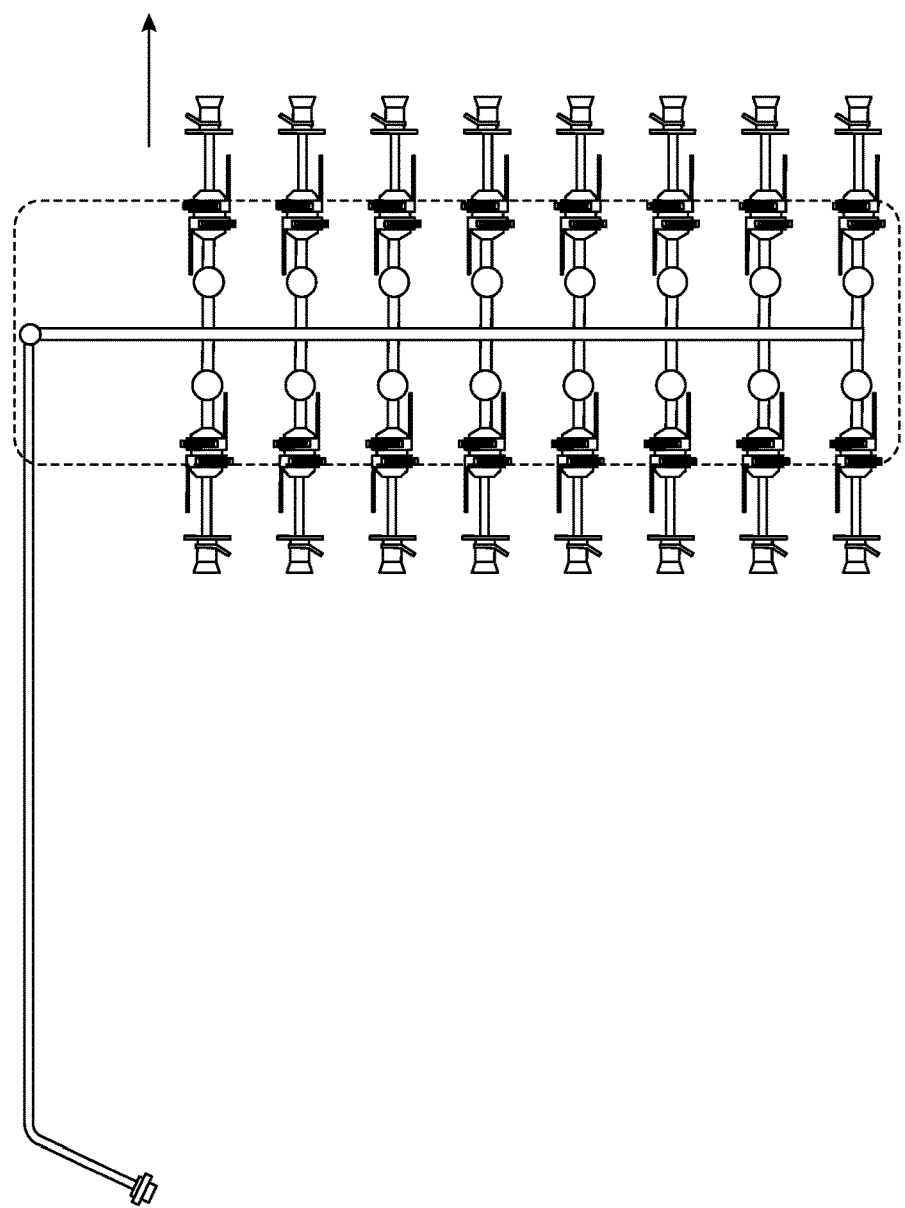
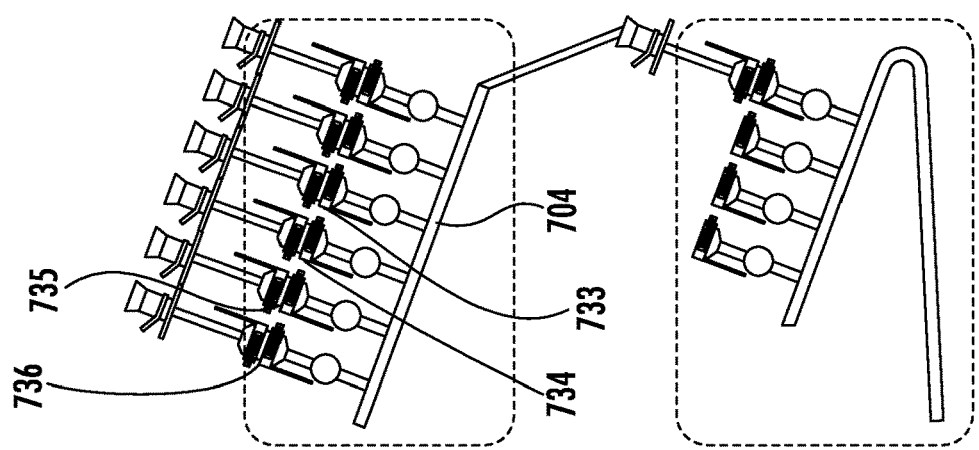
FIG. 26

FLUID DISTRIBUTION SYSTEM WITH SINGLE USE MANIFOLD ASSEMBLY FOR SCALED FILLING

CROSS-REFERENCE TO RELATED APPLICATIONS

This patent application claims the benefit of priority to U.S. Provisional Patent Application No. 63/295,483, filed Dec. 30, 2021, and entitled, "Fluid Distribution System with Single Use Manifold Assembly for Scaled Filling," which is incorporated in its entirety herein by this reference.

BACKGROUND OF THE INVENTION

The use of a single-use system (SUS), such as, for example, biocontainer bags and the like, is becoming more widespread for biopharmaceutical applications. An SUS can be used in systems such as bioreactors and mixing systems. Exemplary upstream SUS applications include media preparation processes such as mixing and filtration, including tangential flow filtration (TFF), for example. Examples of downstream SUS applications include chromatography concentration and diafiltration and buffer preparation, for example.

The adoption of an SUS can offer several advantages over conventional reusable stainless steel systems. Single-use technology can increase process flexibility and reduce cross contamination risks; reduce or even eliminate the need for cleaning; reduce requirements for in-house sterilization, such as by autoclaving, and cleaning chemical inventory; and lower process downtime.

An aspect of biopharmaceutical processing involves managing the movement of liquid through a myriad of elements including tubing, valves and sensors. There is a requirement particularly with a bulk filling process to aliquot fluids from a large container to multiple individual containers while maintaining sterility.

Conventional systems available on the market include a manifold with a fixed number of outlets, and do not allow for scalability. If, for instance, the requirement is to fill twenty containers from a single large tank, a conventional system would include a manifold with a single inlet and twenty outlets. This arrangement allows for filling in a sterile manner, but is limited to a maximum of twenty container fills per manifold.

There is a continued need in the art for single use applications related to the distribution of fluid from a supply to a number of smaller containers. For example, there is a continued need in the art to provide additional solutions for aliquoting liquid in a sterile manner to a substantial number of outlets, and hence containers such as bags and bottles.

It will be appreciated that this background description has been created to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

BRIEF SUMMARY OF THE INVENTION

The present disclosure, in one aspect, is directed to embodiments of a fluid distribution system. In one embodiment, a fluid distribution system includes a first single use distributor manifold, a skid, a first distributor valve arrangement, and a set of single use filler manifolds. The first single use distributor manifold has a first distributor manifold inlet and a plurality of first distributor manifold outlets in fluid communication with the first distributor manifold inlet. The skid includes a pump. The first single use distributor manifold is removably mounted to the skid and is fluidly arranged with the pump for delivering a supply of fluid to the first distributor manifold inlet. The first distributor valve arrangement includes a plurality of valves mounted to the skid and is arranged with the first single use distributor manifold such that each of the first distributor manifold outlets is independently occludable via a respective one of the valves of the first distributor valve arrangement.

The set of single use filler manifolds corresponds to the number of first distributor manifold outlets. Each single use filler manifold has a filler manifold inlet, a plurality of filler manifold outlets in fluid communication with the filler manifold inlet, and an aseptic fluid connector configured to fluidly connect the filler manifold inlet to one of the plurality of first distributor manifold outlets.

In another aspect, the present disclosure is directed to embodiments of techniques of aseptically distributing fluid. In one embodiment, a method of aseptically distributing fluid includes feeding a fluid into a distributor manifold inlet of a single use distributor manifold. A first supply of the fluid is discharged from a first one of a plurality of distributor manifold outlets of the single use distributor manifold to a filler manifold inlet of a first single use filler manifold via a first aseptic fluid pathway. Portions of the first supply of the fluid are respectively discharged from a plurality of filler manifold outlets of the first single use filler manifold to a respective one of a first set of single use containers respectively aseptically fluidly connected to the plurality of filler manifold outlets of the first single use filler manifold. After the portions of the first supply of the fluid are discharged, the first single use filler manifold is disconnected from the single use distributor manifold.

A second supply of the fluid is discharged from a second one of the plurality of distributor manifold outlets of the single use distributor manifold to a filler manifold inlet of a second single use filler manifold via a second aseptic fluid pathway. Portions of the second supply of the fluid are respectively discharged from a plurality of filler manifold outlets of the second single use filler manifold to a respective one of a second set of single use containers respectively aseptically fluidly connected to the plurality of filler manifold outlets of the second single use filler manifold.

In another embodiment, a method of aseptically distributing fluid includes feeding a first supply of fluid into a distributor manifold inlet of a first single use distributor manifold. A first supply of fluid is discharged from a first one of a plurality of distributor manifold outlets of the first single use distributor manifold to a distributor manifold inlet of a second single use distributor manifold via a first aseptic fluid pathway. The first supply of fluid is discharged from a first one of a plurality of distributor manifold outlets of the second single use distributor manifold to a filler manifold inlet of a first single use filler manifold via a second aseptic fluid pathway. Portions of the first supply of fluid are respectively discharged from a plurality of filler manifold outlets of the first single use filler manifold to a respective one of a first set of single use containers respectively aseptically fluidly connected to the plurality of filler manifold outlets of the first single use filler manifold. After the portions of the first supply of fluid are discharged, the first single use filler manifold is disconnected from the second single use distributor manifold.

A second single use filler manifold is connected to a second one of the plurality of distributor manifold outlets of the second single use distributor manifold via a third aseptic fluid pathway. A second supply of fluid is fed into the distributor manifold inlet of the first single use distributor manifold. The second supply of fluid is discharged from the first one of the plurality of distributor manifold outlets of the first single use distributor manifold to the distributor manifold inlet of the second single use distributor manifold via the first aseptic fluid pathway. The second supply of fluid is discharged from a second one of the plurality of distributor manifold outlets of the second single use distributor manifold to a filler manifold inlet of the second single use filler manifold via the third aseptic fluid pathway. Portions of the second supply of fluid are respectively discharged from a plurality of filler manifold outlets of the second single use filler manifold to a respective one of a second set of single use containers respectively aseptically fluidly connected to the plurality of filler manifold outlets of the second single use filler manifold.

Further and alternative aspects and features of the disclosed principles will be appreciated from the following detailed description and the accompanying drawings. As will be appreciated, the fluid distribution systems and the methods of aseptically distributing fluid disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

BRIEF DESCRIPTION OF THE SEVERAL VIEWS OF THE DRAWINGS

FIGS. 13-33 are schematic views of a series of filling steps of an embodiment of a method of aseptically distributing fluid following principles of the present disclosure.

Figure 1:
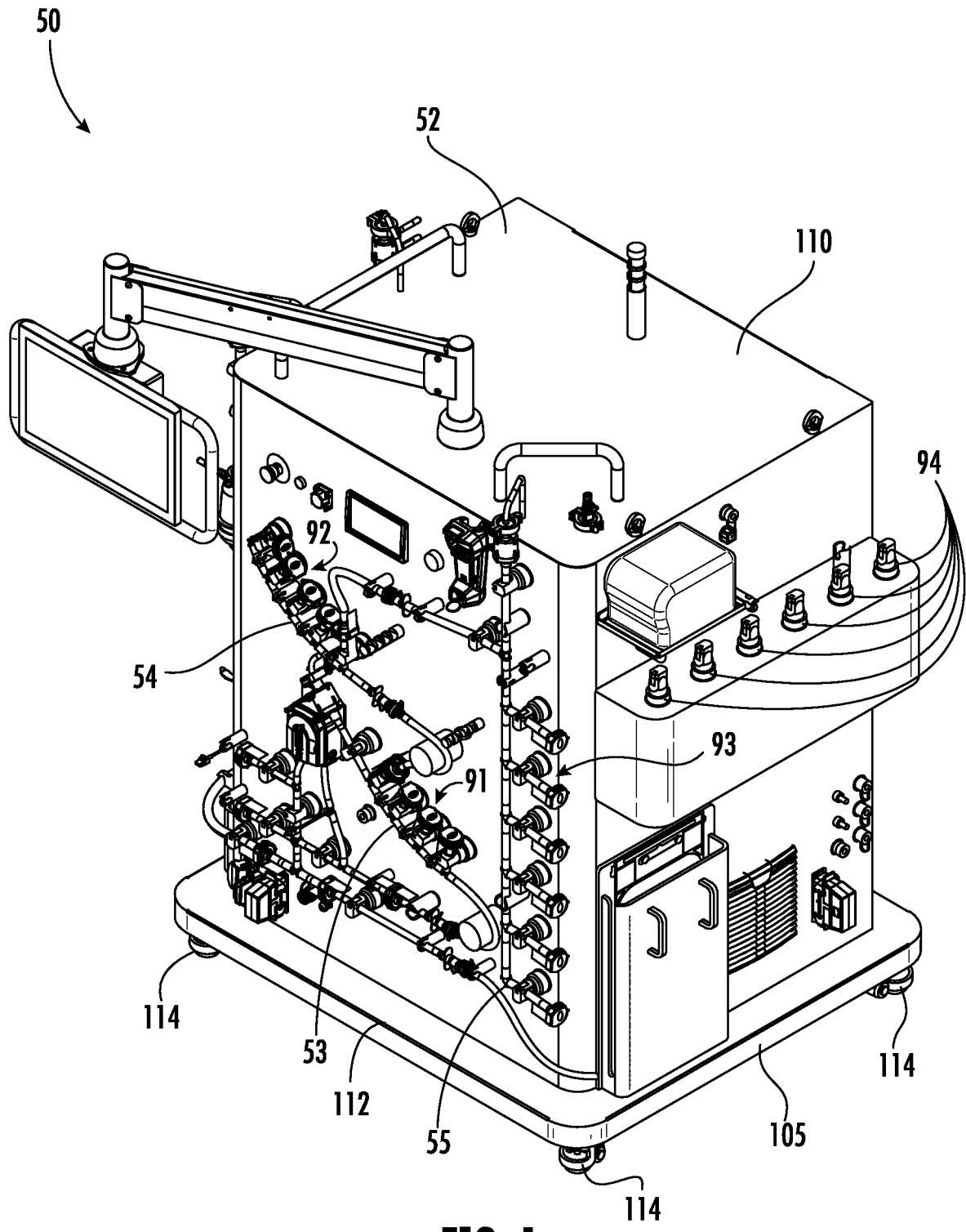
FIG. 1 is a perspective view of an embodiment of a fluid distribution system constructed in accordance with principles of the present disclosure in the form of an embodiment of a distributor skid constructed in accordance with principles of the present disclosure.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF THE INVENTION

Embodiments of a fluid distribution system constructed in accordance with principles of the present disclosure are adapted to be used with embodiments of a method of aseptically distributing fluid following principles of the present disclosure. Embodiments of a fluid distribution system constructed in accordance with principles of the present disclosure can be used in biopharmaceutical environments, and can be used in other industrial applications where different fluids, solutions, reagents and/or chemicals are stored for metering to a process station.

For example, embodiments of a fluid distribution system constructed in accordance with principles of the present disclosure are adapted to be used in a bioprocessing system in which a supply of fluid is distributed to a plurality of containers for use in a bioprocessing application. Embodiments of a fluid distribution system constructed in accordance with principles of the present disclosure can be used to perform applications related to bulk filling in pharmaceutical drug production. Embodiments of a fluid distribution system constructed in accordance with principles of the present disclosure can be used to perform applications related to formulating, filling, and other applications related to aliquoting liquids in a sterile manner.

In embodiments, the fluid distribution system includes a scalable series of single use manifolds in serial fluid communication with each other in a closed, sterile system. In embodiments, the fluid distribution system includes two, three, or more single use manifolds fluidly connected together in series to effectively increase the number of containers that can be filled in a sterile manner via the foremost upstream single use manifold to a number greater than the number of outlets present therein. The number of containers that can be filled using a fluid distribution system constructed according to principles of the present disclosure is therefore scalable to satisfy the particular parameters of a given application.

In embodiments, the fluid distribution system includes a single use distributor manifold adapted for sequential aseptic fluid connection with a set of single use filler manifolds corresponding to the number of distributor manifold outlets. In embodiments, each manifold comprises a replaceable part that is installed in the fluid distribution system for single use in a bioprocessing application and uninstalled after its intended single use for disposal thereof. In embodiments, the fluid distribution system includes an upstream single use distributor manifold adapted for sequential aseptic fluid connection with a set of intermediary single use distributor manifolds corresponding to the number of distributor manifold outlets of the upstream single use distributor manifold. The system also includes multiple sets of single use filler manifolds in which each respective set corresponds to the number of distributor manifold outlets of a respective one of the set of intermediary distributor manifolds.

In embodiments, the fluid distribution system is incorporated into a distributor skid including at least one single use distributor manifold and a set of single use filler manifolds adapted to be placed in fluid communication with one of a plurality of distributor manifold outlets. In yet other embodiments, the fluid distribution system is incorporated into a distributor skid and one or more distribution towers in which the distribution tower is adapted to receive one of a set of single use filler manifolds.

Embodiments of a fluid distribution system constructed in accordance with principles of the present disclosure are configured as a relatively compact solution to achieve a scalable range of different fluid distributing solutions for an intended use in a bioprocessing application. Embodiments of a fluid distribution system constructed in accordance with principles of the present disclosure can include a supply of fluid, at least one single use distributor manifold, a set of single use filler manifolds each having a filler manifold inlet adapted to be placed in fluid communication with one of a plurality of distributor manifold outlets and a plurality of filler manifold outlets, and multiple containers corresponding to the product of the number of filler manifold outlets and the number of single use filler manifolds in the set. Multiple sets of containers can be respectively filled with each of the set of single use filler manifolds in a relatively small footprint (particularly relative to a conventional distribution tower configured for use in a similar bioprocessing application) for storing therein fluid for use in a predetermined bioprocessing application. The containers can be delivered to a storage area (such as, for example, a workstation supporting a plurality of biocontainer bags for use in a bioprocessing application (such as, for example, a chromatography/tangential flow filtration (TFF) application, for example) on demand. Embodiments of a fluid distribution system constructed in accordance with principles of the present disclosure can be used as a replacement for conventional systems for a comparable bioprocessing application that use one single use manifold at a time for filling no more containers than the number of outlets of the single use manifold.

Figure 2:
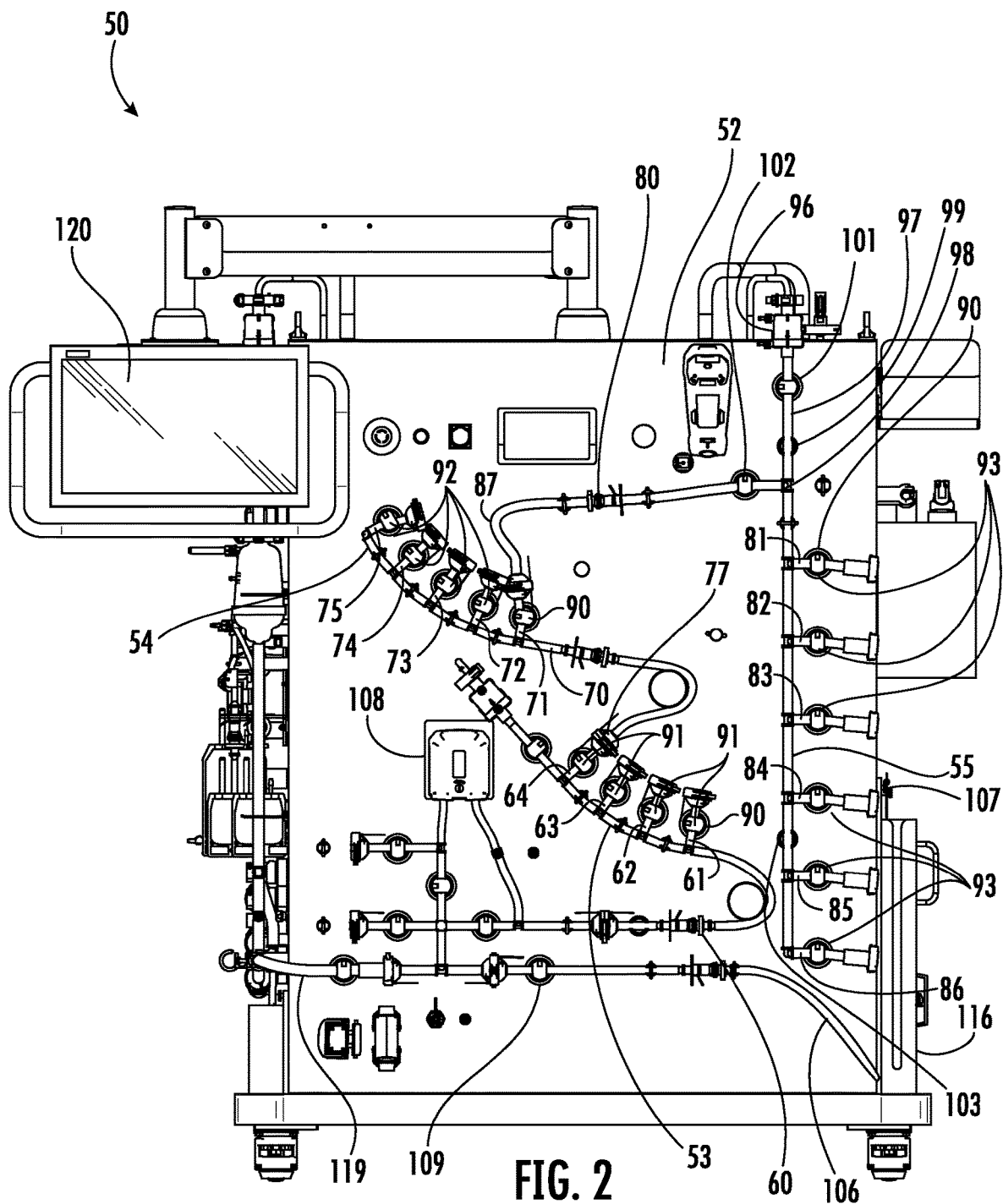
FIG. 2 is an elevational view of the distributor skid of FIG. 1.

Turning now to the FIGURES, there is shown in FIGS. 1 and 2 an embodiment of a fluid distribution system 50 constructed in accordance with principles of the present disclosure that is incorporated into a distributor skid 52 constructed in accordance with principles of the present disclosure that includes an upstream single use distributor manifold 53, an intermediary single use distributor manifold 54, and a single use filler manifold 55 fluidly connected together in series. The distributor skid 52 includes a pump 57 (see FIG. 3) configured to draw fluid from a supply of fluid (not shown) and deliver it to the manifolds 53-55 which are connected in series.

In the illustrated embodiment, each manifold 53-55 comprises a replaceable part that is installed once in the distributor skid 52 for use in a bioprocessing application and uninstalled thereafter for disposal thereof. After completing its intended use in the bioprocessing application, the respective manifold 53-55 can be disconnected from the distributor skid 52 according to a predetermined hierarchy and replaced with another single use manifold having a similar construction.

In embodiments, the fluid distribution system 50 can be used with any suitable fluid, which can be stored in a suitable container, such as a tote, for example, which is in fluid communication with the pump 57. In embodiments, a fluid distribution system 50 constructed in accordance with principles of the present disclosure can include at least two single use manifolds fluidly 54, 55 connected together in series.

The intermediary single use distributor manifold 54 is one of a set of intermediary single use distributor manifolds 54 that have substantially the same construction and are configured to be sequentially mounted to the distributor skid 52. Similarly, the single use filler manifold 55 is one of a set of single use filler manifolds 55 that have substantially the same construction are configured to be sequentially mounted to the distributor skid 52. The illustrated fluid distribution system 50 is configured to receive fluid (such as, buffer solutions for use in an intended bioprocessing application, e.g., chromatography, TFF, etc.) from a supply and serially distribute the fluid to as many as one hundred twenty containers sequentially using the sets of single use filler manifolds 55 and single use distributor manifolds 54 before replacing the upstream single use distributor manifold 53 and opening the closed system (six outlets for each one of the set of twenty single use filler manifolds 55×five outlets for each one of the set of four intermediary single use distributor manifolds 54×four outlets of the upstream single use distributor manifold 53).

In other embodiments, the fluid distribution system 50 can be configured to fill a different maximum number of containers in a closed system before it would need to be opened to continue distributing fluid to more containers. In embodiments, the set of intermediary single use distributor manifolds 54 can include at least one manifold having a construction different from at least one other manifold of the set (e.g., a different number of outlets), and, in embodiments, the set of single use filler manifolds 55 can include at least one manifold having a construction different from at least one other manifold of the set (e.g., a different number of outlets).

Referring to FIG. 2, each of the upstream single use distributor manifold 53, the intermediary single use distributor manifold 54, and the single use filler manifold 55 can have a similar construction. In the illustrated embodiment, each manifold 53-55 includes a tubing arrangement that interconnects the various ports of the manifold and is associated with control valves to control the flow of fluid through the manifold. In embodiments, the tubing arrangement comprises a plurality of flexible tubing lines adapted to be selectively occluded by a pinch valve externally mounted thereto. In embodiments, the flexible tubing can be made from any suitable material, such as, silicone, thermoplastic elastomer (TPE), etc.

In embodiments, the manifolds 53-55 can be made from any suitable material and can comprise suitable tubing defining fluid conduits therethrough. In embodiments, the manifolds 53-55 comprise any one of a range of suitable materials and assemblies as will be readily known to one of ordinary skill in the art, such as, e.g., silicone tubing, plastic injection molded adapters, and commercially-available connectors and disconnectors (e.g., Kleenpack® Presto sterile connectors and Kleenpack® sterile disconnectors from Pall Corporation of New York). The illustrated manifolds 53-55 are made from tubing that can be selectively occluded by a pinch valve.

The upstream single use distributor manifold 53 is removably mounted to the distributor skid 52. The upstream single use distributor manifold 53 has an upstream distributor manifold inlet 60 and a plurality of upstream distributor manifold outlets 61, 62, 63, 64 in fluid communication with the upstream distributor manifold inlet via the hollow body of the manifold 53. The illustrated upstream single use distributor manifold 53 includes four upstream distributor manifold outlets 61-64. In other embodiments, the number of upstream distributor manifold outlets 61-64 can be different. The upstream distributor manifold inlet 60 is fluidly arranged, via suitable tubing and connectors, with the pump 57 mounted to the distributor skid 52 for delivering the supply of fluid to the series of manifolds 53-55.

The intermediary single use distributor manifold 54 is removably mounted to the distributor skid 52. The intermediary single use distributor manifold 54 has an intermediary distributor manifold inlet 70 and a plurality of intermediary distributor manifold outlets 71, 72, 73, 74, 75 in fluid communication with the intermediary distributor manifold inlet 70 via the hollow body of the manifold 54. The intermediary distributor manifold inlet 70 is in fluid communication with one of the upstream distributor manifold outlets, in this case the fourth distributor manifold outlet 64. The illustrated intermediary single use distributor manifold 54 includes five intermediary distributor manifold outlets 71-75. In other embodiments, the number of intermediary distributor manifold outlets 71-75 can be different.

The intermediary single use distributor manifold 54 is one of a set of intermediary single use distributor manifolds 54. The set of intermediary single use distributor manifold 54 corresponds to the number of upstream distributor manifold outlets 61-64, in this case four. Each intermediary single use distributor manifold 54 has an aseptic fluid connector 77 configured to fluidly connect the intermediary distributor manifold inlet 70 to one of the upstream distributor manifold outlets. In embodiments, each intermediary single use distributor manifold 54 of the set of intermediary single use distributor manifolds 54 has a similar construction. In embodiments, at least one intermediary single use distributor manifold 54 of the set of intermediary single use distributor manifolds 54 can have a different construction from at least one other of the set, such as a different number of intermediary distributor manifold outlets from at least one other of the set of intermediary single use distributor manifolds 54.

In embodiments, the distribution manifolds 53, 54 are curved, which allows all connecting tube lengths to be substantially similar. This construction can keep both the manifold length and footprint relatively compact while simplifying the manifold manufacturing process.

The single use filler manifold 55 is removably mounted to the distributor skid 52. The single use filler manifold 55 has a filler manifold inlet 80 and a plurality of filler manifold outlets 81, 82, 83, 84, 85, 86 in fluid communication with the filler manifold inlet 80 via the hollow body of the manifold 55. The filler manifold inlet 80 is in fluid communication with one of the intermediary distributor manifold outlets 71-75, in this case the first intermediary distributor manifold outlet 71. The illustrated single use filler manifold 55 includes six filler manifold outlets 81-86. In other embodiments, the number of filler manifold outlets 81-86 can be different.

The single use filler manifold 55 is one of a set of single use filler manifolds 55. In embodiments, the set of single use filler manifolds 55 corresponds to the product of the number of outlets for each distributor manifold of two or more distributor manifolds connected in series upstream of the filler manifold inlet. In embodiments where only one single use distributor manifold is in series connection with the filler manifold inlet, the set of single use filler manifolds 55 can correspond to the number of distributor manifold outlets of the single distributor manifold. In the illustrated embodiment, the set of single use filler manifolds 55 includes twenty single use filler manifolds 55, which corresponds to the product of the number of intermediary distributor manifold outlets (five) and the number of upstream distributor manifold outlets (four). In embodiments, the set of single use filler manifolds 55 corresponds to at least the number of intermediary distributor manifold outlets. Each single use filler manifold has an aseptic fluid connector 87 configured to fluidly connect the filler manifold inlet 80 to one of the plurality of intermediary distributor manifold outlets 71-75.

In embodiments, each single use filler manifold 55 of the set of single use filler manifolds 55 has a similar construction. In embodiments, at least one single use filler manifold 55 of the set of single use filler manifolds 55 can have a different construction from at least one other of the set, such as a different number of filler manifold outlets from at least one other of the set of single use filler manifolds 55.

Referring to FIG. 2, the illustrated fluid distribution system 50 includes a valve 90 associated with each outlet of the manifolds 53-55 (only the first of which is marked in FIG. 2). An upstream distributor valve arrangement 91 includes a plurality of valves 90 mounted to the skid 52 and arranged with the upstream single use distributor manifold 53 such that each of the upstream distributor manifold outlets 61-64 is independently occludable via a respective one of the valves 90 of the upstream distributor valve arrangement 91. An intermediary distributor valve arrangement 92 includes a plurality of valves 90 mounted to the skid 52 and arranged with the intermediary single use distributor manifold 54 such that each of the intermediary distributor manifold outlets 71-75 is independently occludable via a respective one of the valves 90 of the intermediary distributor valve arrangement 92. A filler valve arrangement 93 includes a plurality of valves 90 mounted to the skid 52 and arranged with the single use filler manifold 55 such that each of the filler manifold outlets 81-86 is independently occludable via a respective one of the valves 90 of the filler valve arrangement 93.

In embodiments, the valve arrangements 91-93 can comprise any suitable valve adapted to selectively occlude the outlet with which it is associated. In the illustrated embodiment, the valve arrangements 91-93 include pinch valves adapted to control the flow of fluid within the system by occluding the tubing of the manifold to effectively occlude the manifold outlet with which it is associated. The valves 90 are secured to the skid 52 and provide the means for removable mounting the manifolds 53-55 to the skid 52. In other embodiments, a different type of valve can be used, as will be readily familiar to one skilled in the art, such as a solenoid valve, for example. In embodiments, the valves 90 can be operated by a suitable source, such as, a pneumatic source or an electrical power source, for example. In embodiments, the operation of the valves 90 of the valve arrangements 91-93 can be coordinated using a control unit which is suitably programmed to operate one or more desired fluid distributing sequences.

Referring to FIG. 1, the illustrated distributor skid 52 includes a first filler valve arrangement 93 and a second filler valve arrangement 94. The first filler valve arrangement 93 is disposed on a side of the distributor skid 52 including the upstream and intermediary distributor manifolds 53, 54. The second filler valve arrangement 94 is disposed on another side of the distributor skid 52.

Figure 3:
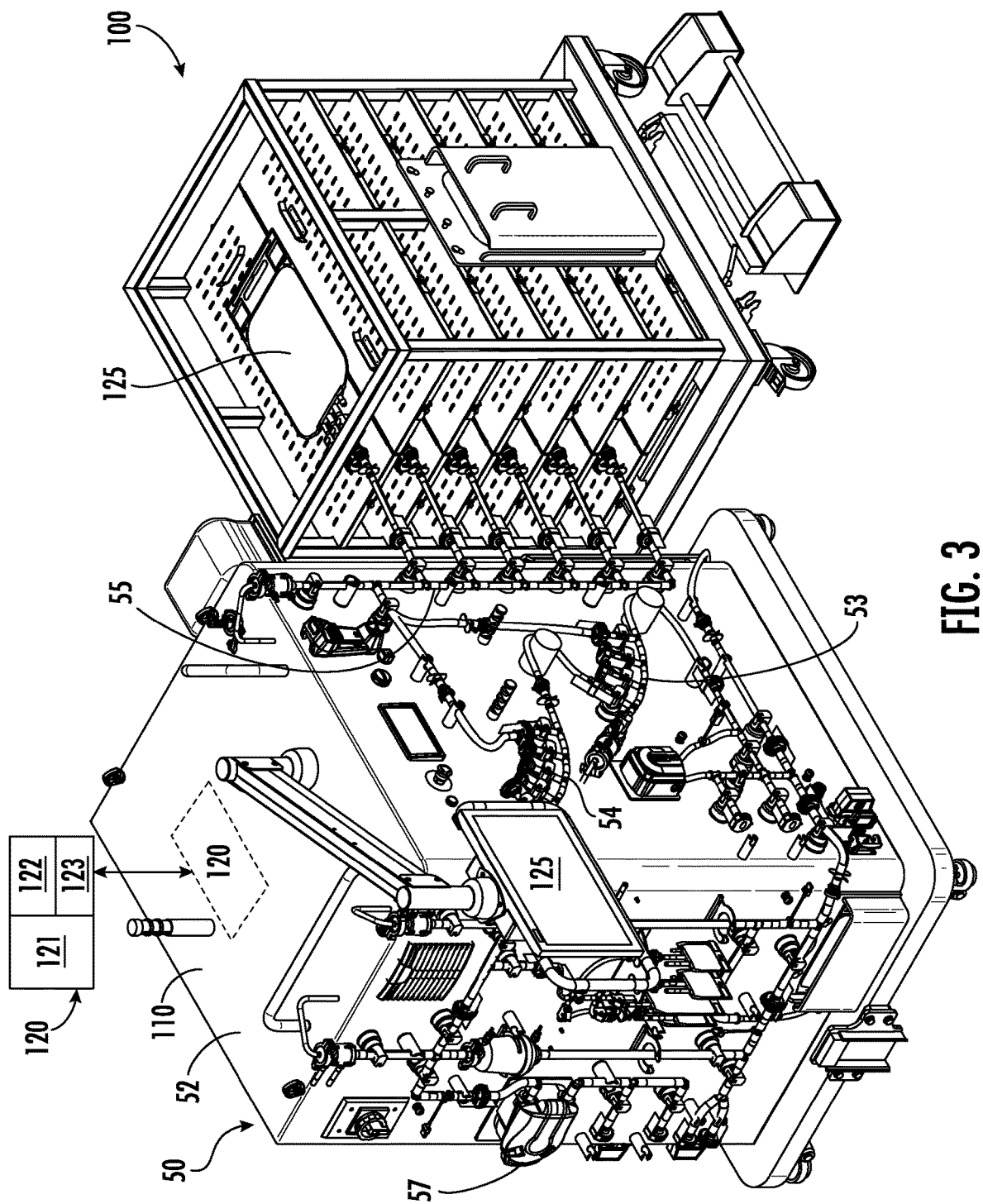
FIG. 3 is another perspective elevational view of the distributor skid of FIG. 1 and a perspective view of an embodiment of a workstation configured to hold a plurality of single use containers for receiving aliquoted portions of fluid from the fluid distribution system.

The valves of the first filler valve arrangement 93 are disposed along a vertical axis in spaced relationship to each other. The single use filler manifold 55 is mounted to the distributor skid 52 such that the valves of the first filler valve arrangement 93 are respectively associated with each one of the filler manifold outlets. This arrangement is particularly useful in filling containers stored in a workstation 100 configured as shown in FIG. 3.

Figure 5:
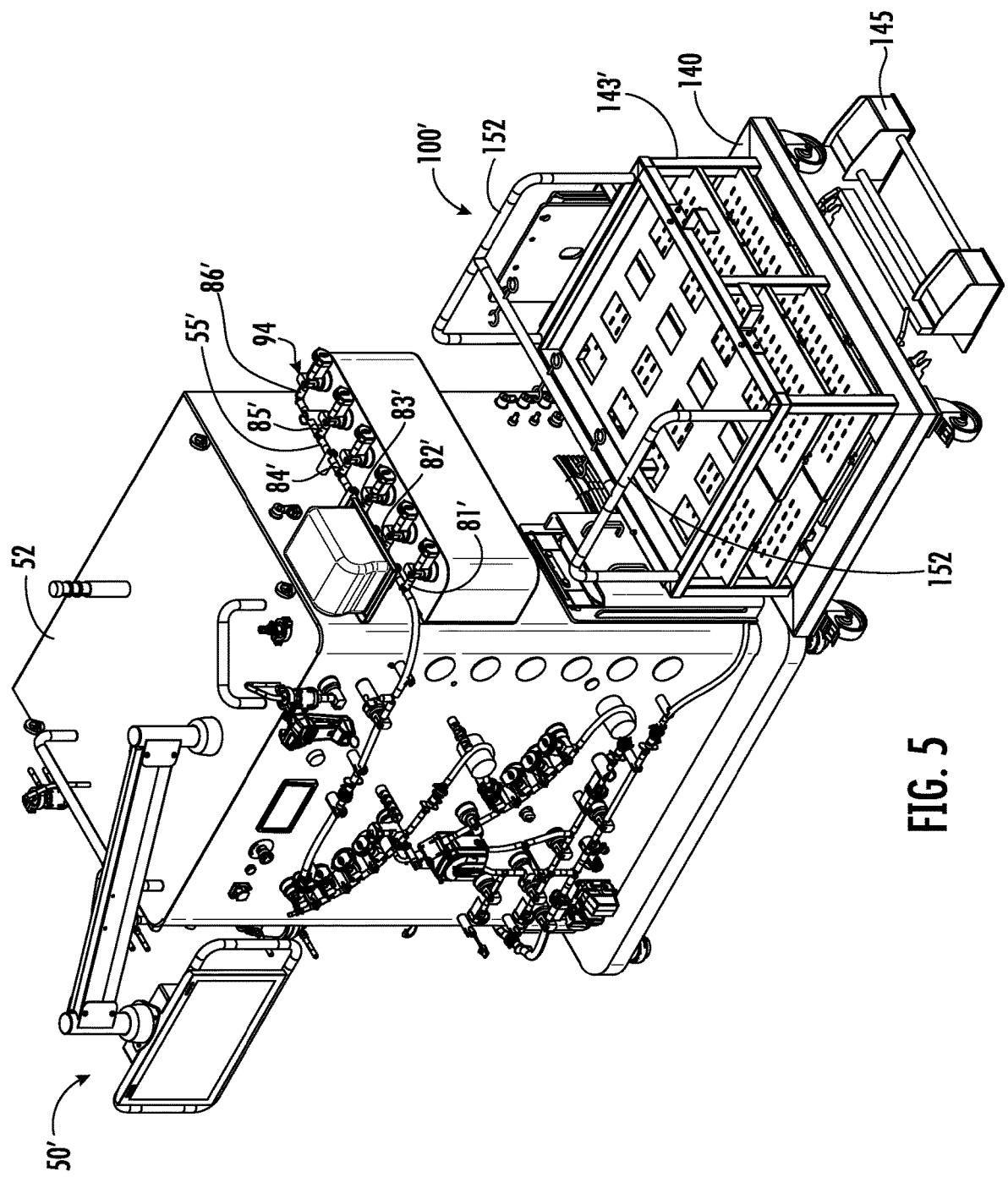
FIG. 5 is another perspective elevational view of the distributor skid of FIG. 1, including another embodiment of a fluid distribution system constructed in accordance with principles of the present disclosure, and a perspective view of another embodiment of a workstation configured to hold a plurality of single use containers for receiving aliquoted portions of fluid from the fluid distribution system.

The valves of the second filler valve arrangement 94 are disposed along a horizontal axis in spaced relationship to each other. A single use filler manifold 55' as shown in FIG. 5 can be mounted to the distributor skid 52 such that the valves of the second filler valve arrangement 94 are respectively associated with each one of the filler manifold outlets. This arrangement is particularly useful in filling containers stored in a workstation 100' configured as shown in FIG. 5.

Referring to FIG. 1, the distributor skid 52 includes a trolley 105, a cabinet 110, the single use manifolds 53-55, and the valve arrangements 91-94. The cabinet 110 is mounted atop the trolley 105 and is configured to house hydraulic and automation equipment of the liquid distribution system 50. The manifolds 53-55 comprise single use manifolds that are removably mounted to the cabinet 110 such that the manifolds 53-55 are is in operable arrangement with the valves of the valve arrangements 91-93 mounted to the cabinet 110.

The trolley 105 includes a base 112 and a plurality of wheels 114 rotatably attached to the base 112. In the illustrated embodiment, the base 112 is rectangular, and there is a wheel 114 rotatably attached at each corner of the base 112. In embodiments, the base 112 can be substantially square-shaped.

The cabinet 110 is mounted to the base 112 of the trolley 105. In embodiments, the cabinet 110 comprises a storage unit for automation and hydraulic equipment and is made from a suitable metal, such as stainless steel, for example. The cabinet 110 defines an interior cavity which can be suitably configured for storing and supporting components of the liquid distribution system. The valves of the valve arrangements 91-94 can be supported by the cabinet 110. In the illustrated embodiment, a clamping portion of each valve projects from an exterior surface of the cabinet 110 for being respectively associated with a manifold outlet.

Referring to FIG. 3, in embodiments, the cabinet 110 houses therein a control unit 120 and at least one pump body 57. The pump 57 is in operable relationship with the control unit 120 such that the control unit 120 can selectively operate the pump 57. The pump 57 is adapted to selectively produce a flow of fluid to deliver a supply of fluid to the manifolds 53-55. In embodiments, the pump 57 can be any suitable pump capable of producing a flow of fluid through the manifolds for delivery to the single use containers 125 connected to the filler manifold 55 and that meets the specification of the intended application. In embodiments, the pump 57 comprises a variable displacement pump. In embodiments, the fluid distribution system 50 includes a plurality of pumps which can be used to delivery one or more types of fluid to the manifolds 53-55.

In embodiments, the control unit 120 can comprise any suitable equipment configured to control the operation of at least one component of the liquid distribution system 50 when performing a filling operation. In embodiments, the control unit 120 includes a processor 121, a non-transitory computer readable medium 122 bearing a fluid distribution program, a data storage device 123, and a display device 125. The processor 121 is arranged with the computer readable medium 122 to execute the fluid distribution program. The processor 121 is in operable arrangement with the display device 125 to selectively display output information from the fluid distribution program and/or to receive input information from a graphical user interface displayed by the display device 125.

The processor 121 can be configured to act as a controller to selectively operate at least one component of the fluid distribution system 50, such as the pump 57 and the valve arrangements, for example. In embodiments, the processor 121 is in electrical communication with the pump(s) and the valve arrangements to selectively operate the valves based upon instructions from the fluid distribution program.

In embodiments, a controller and the processor 121 can comprise separate devices, and the controller can be in operable communicative arrangement with the processor 121. In embodiments, the controller can include a user input and/or interface device having one or more user-actuated mechanisms (e.g., one or more push buttons, slide bars, rotatable knobs, a keyboard, and a mouse) adapted to generate one or more user actuated input control signals. In embodiments, the controller can be configured to include one or more other user-activated mechanisms to provide various other control functions for the fluid distribution system, as will be appreciated by one skilled in the art. The controller can be associated with the display device 125 which is adapted to display a graphical user interface. The graphical user interface can be configured to function as both a user input device and a display device in embodiments. In embodiments, the display device 125 can comprise a touch screen device adapted to receive input signals from a user touching different parts of the display screen. In embodiments, the controller can be in the form of a smart phone, a tablet, a personal digital assistant (e.g., a wireless, mobile device), a laptop computer, a desktop computer, or other type of device.

In embodiments, the fluid distribution program has a scaling module configured to sequentially progress through a series of valve open-closed conditions to carry out a filling sequence according to principles of the present disclosure. For example, the scaling module can be configured to open a respective one of the upstream distributor manifold outlets and the intermediary distributor manifold outlets and close the other of upstream distributor manifold outlets and the intermediary distributor manifold outlets to perform a corresponding sequential series of filling operations with a respective one of the set of single use filler manifolds. The scaling module can sequence through an open condition for each one of the intermediary distributor manifold outlets with the one of the upstream distributor manifold outlets in the open condition, and then close that one of the upstream distributor manifold outlets and put a second one of the upstream distributor manifold outlets in the open condition while the others are closed. The scaling module can orchestrate sequential filling operations for the rest of the valves in a similar manner. In embodiments, the scaling module includes logic for scaling the filling operations to a desired number of containers for a filling sequence for a given closed system.

In embodiments, the control unit 120 is in electrical communication with each pump 57 used to deliver the fluid(s) to the manifolds 53-55 and with each valve of the valve arrangements 91-94. The control unit 120 is configured to selectively operate the pump 57 and the valves of the valve arrangements 91-94 according to logic and operation parameters contained in the fluid distribution program. In embodiments, the control unit 120 is configured to control at least one of a pump speed and a volume displacement of the pump 57 to control the amount of fluid being dispensed into the single use containers 125 connected to the filler manifold 55. In the illustrated embodiment, the control unit 120 is configured to independently operate each valve of the different valve arrangements 91-93 to place each valve arrangement in a series of sequential valve conditions in order to fill a number of single use containers 125 that is greater than the number of filler manifold outlets of any one of the set of single use filler manifolds 55.

In embodiments, the control unit 120 is configured to selectively operate the pump(s) 57 according to at least one input signal received from each workstation 100 holding the containers 125. In embodiments, the control unit 120 is configured to operate the distributor skid 52 to perform at least one filling sequence.

In embodiments, the processor 121 comprises a specially programmed processor that can be used to fill a series of single use containers 125 using at least one distributor manifold 53, 54 and a set of single use filler manifolds 55. In the illustrated embodiment, the processor 121 is configured to facilitate the control and the operation of the fluid distribution system 50. In embodiments, the processor 121 can be configured to receive input signals from the controller, to send input control signals to the controller, and/or to send output information to the controller. In the illustrated embodiment, the controller and the processor 121 comprise the same device.

In embodiments, the processor 121 is configured to display in the display device 125 fluid data received from at least one sensor in electrical communication with the control unit 121. The fluid data can also be stored in the data storage device 123 operably arranged with the processor 121.

In embodiments, the processor 121 can comprise any suitable computing device, such as, a microprocessor, a mainframe computer, a digital signal processor, a portable computing device, a personal organizer, a device controller, a logic device (e.g., a programmable logic device configured to perform processing functions), a digital signal processing (DSP) device, or a computational engine within an appliance. In embodiments, the processor 121 also includes one or more additional input devices (e.g., a keyboard and a mouse).

The processor 121 can have one or more memory devices associated therewith to store data and information. The one or more memory devices can include any suitable type, including volatile and non-volatile memory devices, such as RAM (Random Access Memory), ROM (Read-Only Memory), EEPROM (Electrically-Erasable Programmable Read-Only Memory), flash memory, etc. In one embodiment, the processor 121 is adapted to execute programming stored upon the non-transitory computer readable medium 122 to perform various methods, processes, and modes of operations in a manner following principles of the present disclosure.

In embodiments, the non-transitory computer readable medium 122 can contain a fluid distribution program that is configured to implement an embodiment of a method of distributing fluid according to principles of the present disclosure. In embodiments, the fluid distribution program includes a graphical user interface that can be displayed by the display device 125. The graphical user interface can be used to facilitate the inputting of commands and data by a user to the fluid distribution program and to display outputs generated by the fluid distribution program.

The fluid distribution program can be stored upon any suitable computer-readable storage medium. For example, in embodiments, a fluid distribution program following principles of the present disclosure can be stored upon a hard drive, floppy disk, CD-ROM drive, tape drive, zip drive, flash drive, optical storage device, magnetic storage device, and the like.

In embodiments, the processor 121 is in operable communication with the data storage device 123 which includes at least one database containing fluid distribution data. In embodiments, the fluid distribution program can be configured to store the fluid distribution data generated during operation of the system in the data storage device 123. In embodiments, the fluid distribution data can be associated in a logical manner with time data in the data storage device such that the various data can be retrievable for a given time.

Figure 4:
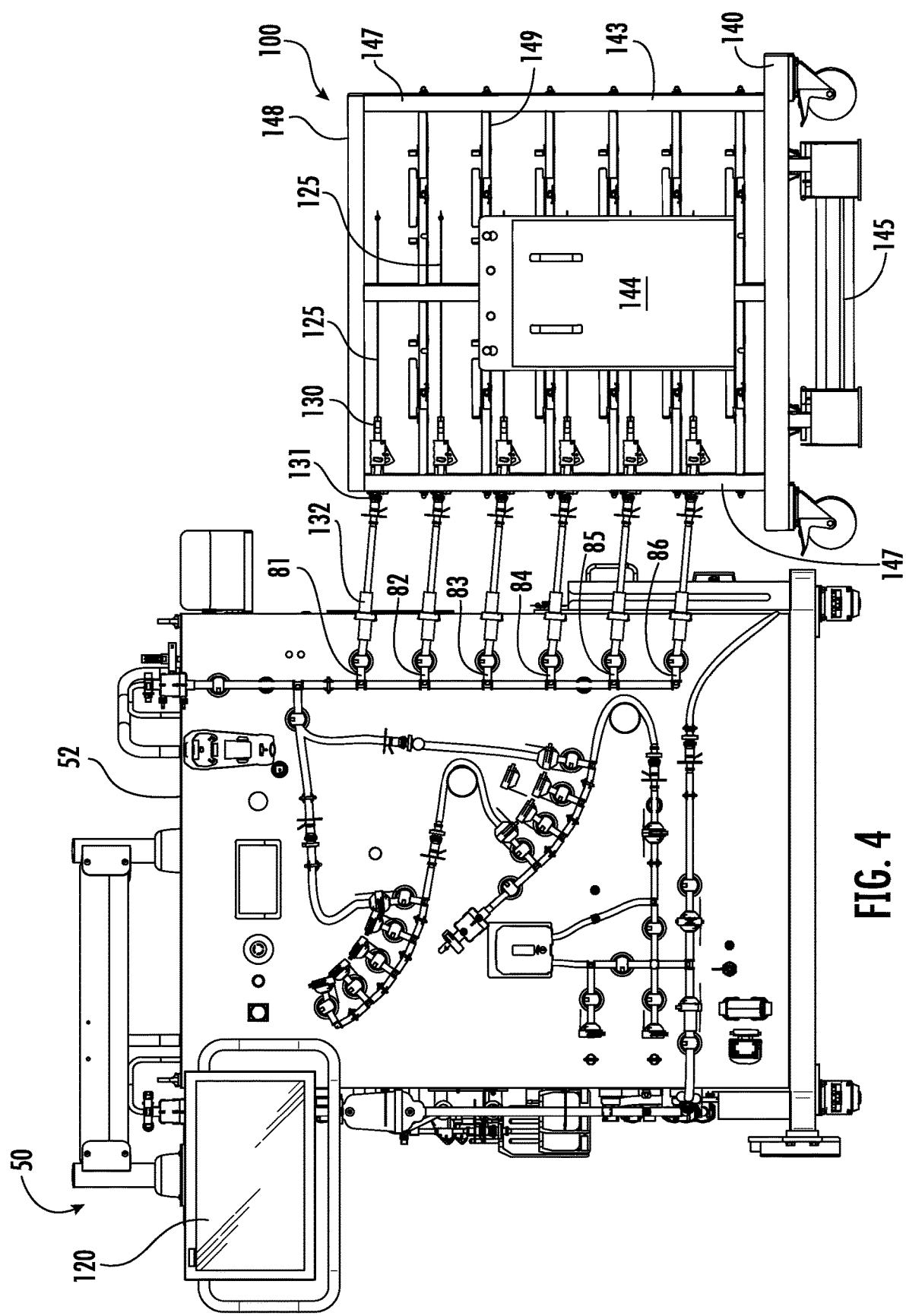
FIG. 4 is an elevational view of the distributor skid and the workstation of FIG. 4.

Referring to FIG. 4, the workstation 100 is configured to hold a plurality of single use containers 125. Each single use container 125 has an access port 130 which is fluidly connected to a respective one of the filler manifold outlets 81-86 via an aseptic fluid disconnector 131 and an aseptic fluid connector 132.

The workstation 100 comprises a workstation configured to hold fluid in the singles use containers 125 that the fluid distribution system aliquoted from a larger supply. The workstation 100 includes a trolley 140, a frame structure 143, and a weigh scale 145.

The frame structure 143 is mounted to the trolley 140 and is configured to support the single use containers 125 in a stacked relationship. The frame structure 143 includes four uprights 147 connected to a respective corner of the trolley 140 and in spaced relationship to each other and four cross members 148 each extending between two of the uprights 147 such that the frame structure 143 has a rectangular configuration. In the illustrated embodiment, the workstation includes six shelves 149 that are each configured to support at least one single use container 125 such that the frame structure 143 can support single use containers 125 in a vertical stacked relationship to each other. In other embodiments, the workstation 100 can be configured to support a different number of single use containers 125, including having shelves 149 each configured to support multiple single use containers 125.

The trolley 140 includes a base and a plurality of wheels rotatably attached to the base. In the illustrated embodiment, the base is rectangular, and there is a wheel rotatably attached at each corner of the base. In embodiments, the base can be substantially square-shaped. The base of the trolley 140 is mounted to a bottom of the frame structure 143. The trolley 140 is positionable over the weigh scale 145 such that the weigh scale 145 supports the weight of the trolley 140 (and thus also the frame structure 143 and the containers 125 stored therein).

In embodiments, the weigh scale 145 can be any suitable scale suitable for weighing loads in a range corresponding to the intended fluid application. In embodiments, the weigh scale 145 comprises a suitable load cell which generates an electrical signal indicative of the measured weight. The weigh scale 145 can be configured to generate a weight signal and can be placed in electrical communication with the control unit 120 to transmit the weight signal to the control unit 120. The control unit 120 can use the weight signal to provide a feedback loop to the control unit 120 to verify the intended amount of fluid is dispensed to the containers 125 stored in the workstation 100. In embodiments, the control unit 120 can be configured to convert the measured weight of the fluid into a volume measurement for such fluid.

In other embodiments, a workstation suitable for use with a fluid distribution system constructed according to principles of the present disclosure can have a different construction. For example, in other embodiments, the volume/weight of the containers 125 can be monitored using other techniques, as will be appreciated by one skilled in the art, such as a fill level sensor. In embodiments, the fill level sensor is configured to generate a fill level signal indicative of the amount of material within the storage volume of the single use container as detected by the fill level sensor. Each fill level sensor can be place in electrical communication with the control unit so that the control unit can use the fill level signals as a feedback loop. In embodiments, a capacitive fill level sensor can be used to measure the fill level of fluid media or of solid materials disposed within the storage volume of the container. In embodiments, the capacitive fill level sensor can be a suitable commercially-available strip sensor, such as those available from Balluff Ltd., which can detect fill levels along the strip over a predetermined length, such as, e.g., 850 mm. In embodiments, the capacitive fill level sensor for measuring fill levels can be configured to develop a measurement impedance in response to being within detection proximity of the material stored within the single use container, the ohmic component of which, particularly the capacitive component of which, reflects a measure for the fill level of the material within the container and which can be used to generate the fill level signal.

Each of the single use containers 125 is in fluid connection with a respective one of the filler manifold outlets 81-86 of the distributor skid 52 via a flexible tubing line extending between each container 125 and the filler manifold outlet 81-86 with which it is associated, and in which fluid communication is selectively maintained via a respective aseptic connector 132. In embodiments, the aseptic connector 132 can be any suitable connector, such as commercially-available aseptic connectors which will be familiar to those skilled in the art. In embodiments, the tubing which places the containers 125 in fluid communication with the associated filler manifold outlet 81-86 is adapted to be selectively occluded by a pinch valve externally mounted thereto and, in embodiments, comprises flexible tubing made from any suitable material, such as, silicone, thermoplastic elastomer (TPE), etc.

In embodiments, the single use container 125 comprises any suitable container configured to store a predetermined volume of material for use in an intended application. In embodiments, the single use container 125 comprises a "2D" (or "two-dimensional") biocontainer bag, as is familiar to those skilled in the art.

In the illustrated embodiment, the single use container 125 comprises a 2D biocontainer bag made from a flexible film material. The biocontainer bag 125 can include two or more ports and tubing with connector ends that are configured to receive material within the interior storage volume of the bag and/or discharge material from the bag. In other embodiments, the biocontainer bag 125 includes at least one other port configured for use as a sampling port. In embodiments, the biocontainer bag 125 can define therein a storage volume of a predetermined size, such as a volume in a range from one liter to twenty liters, for example. In other embodiments, the storage volume can be a different size, such as, e.g., one hundred liters. In embodiments, the biocontainer bag 125 comprises a suitable commercially-available single use biocontainer bag, such as, for example, those available from Pall Corporation of Port Washington, New York, under the brand name Allegro™ 2D biocontainer bags.

In embodiments, the biocontainer bag 125 can include at least a pair of flexible panels that are connected together. The flexible panels cooperate together to define an interior storage volume that is configured to hold a predetermined volume of material (e.g., one hundred liters). In embodiments, each panel is made from a suitable plastic material. For example, in embodiments, each panel is made of a low density polyethylene (LDPE) fluid contact and external film with an ethylene-vinyl alcohol copolymer (EvOH) gas barrier internal film. In embodiments, the biocontainer bag can be made from a material that satisfies the requirements of at least one of: the USP <88> Biological Reactivity Tests, in vivo, for Class VI-50° C. Plastics that target-monitor the effect of the biocontainer's extracts for their systemic toxicity, tissue irritation, and biocompatibility for implantation; USP <87> Biological Reactivity Tests (in vitro) for plastics (cytotoxicity); and ISO 10993 Biological Evaluation of a Medical Device (Section 8.2.2: ISO 10993 Biological Evaluation of Medical Devices) in Section 4 (Hemolysis), Section 5 (Cytotoxicity), Section 6 (Implantation Test), Section 10 (Irritation and Sensitization Test), and Section 11 (Acute Systemic Toxicity).

Referring to FIG. 5, in embodiments, the fluid distribution system 50' includes a single use filler manifold 55' mounted to the distributor skid 52 such that the valves of the second filler valve arrangement 94 are respectively associated with each one of the filler manifold outlets 81', 82', 83', 84', 85', 86'. The valves of the second filler valve arrangement 94 are disposed in spaced relationship to each other along the horizontal axis. With this arrangement, the filler manifold outlets 81'-86' can be disposed over a workstation 100' configured as shown in FIGS. 5 and 6.

Figure 6:
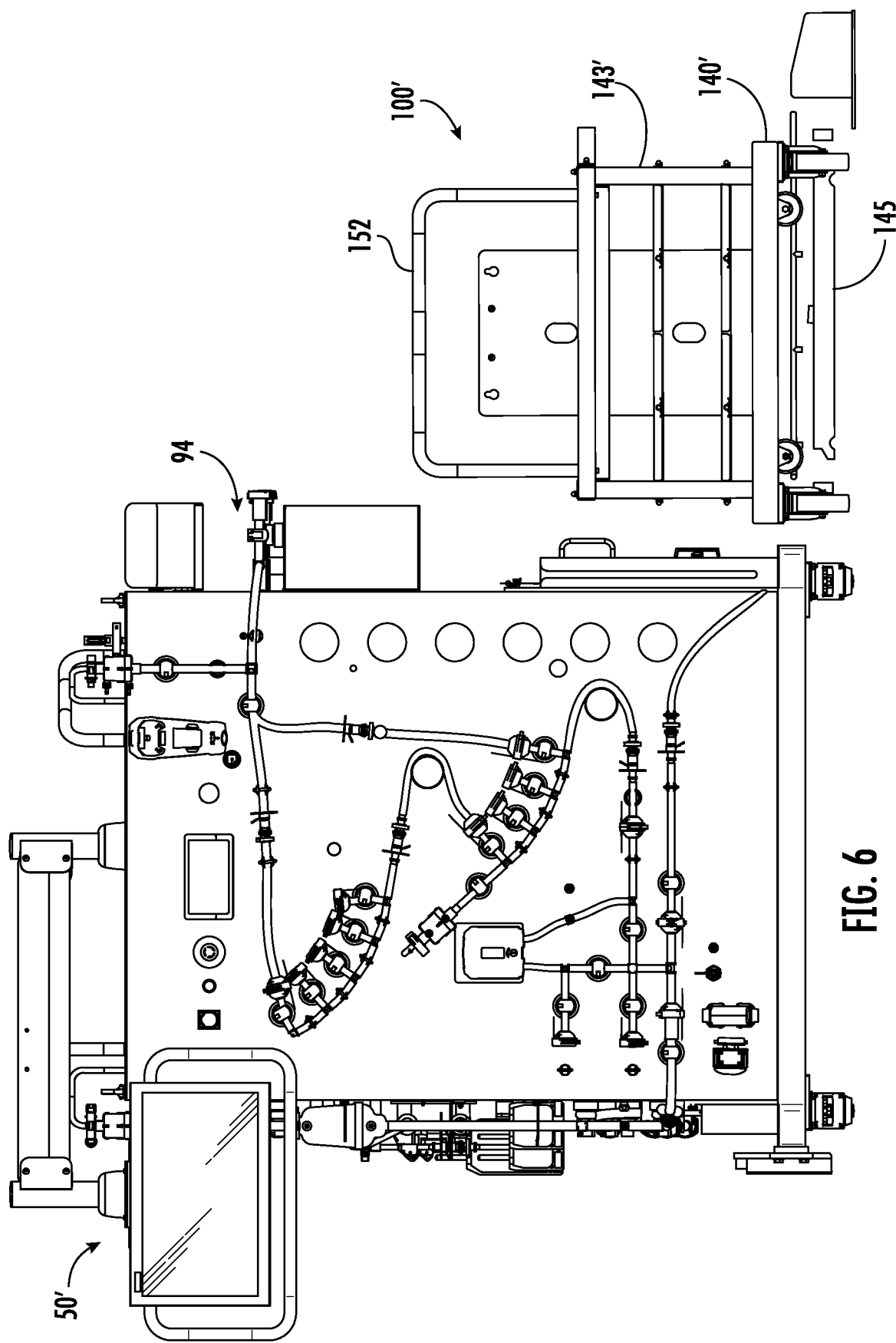
FIG. 6 is an elevational view of the distributor skid and the workstation of FIG. 5.
Figure 7:
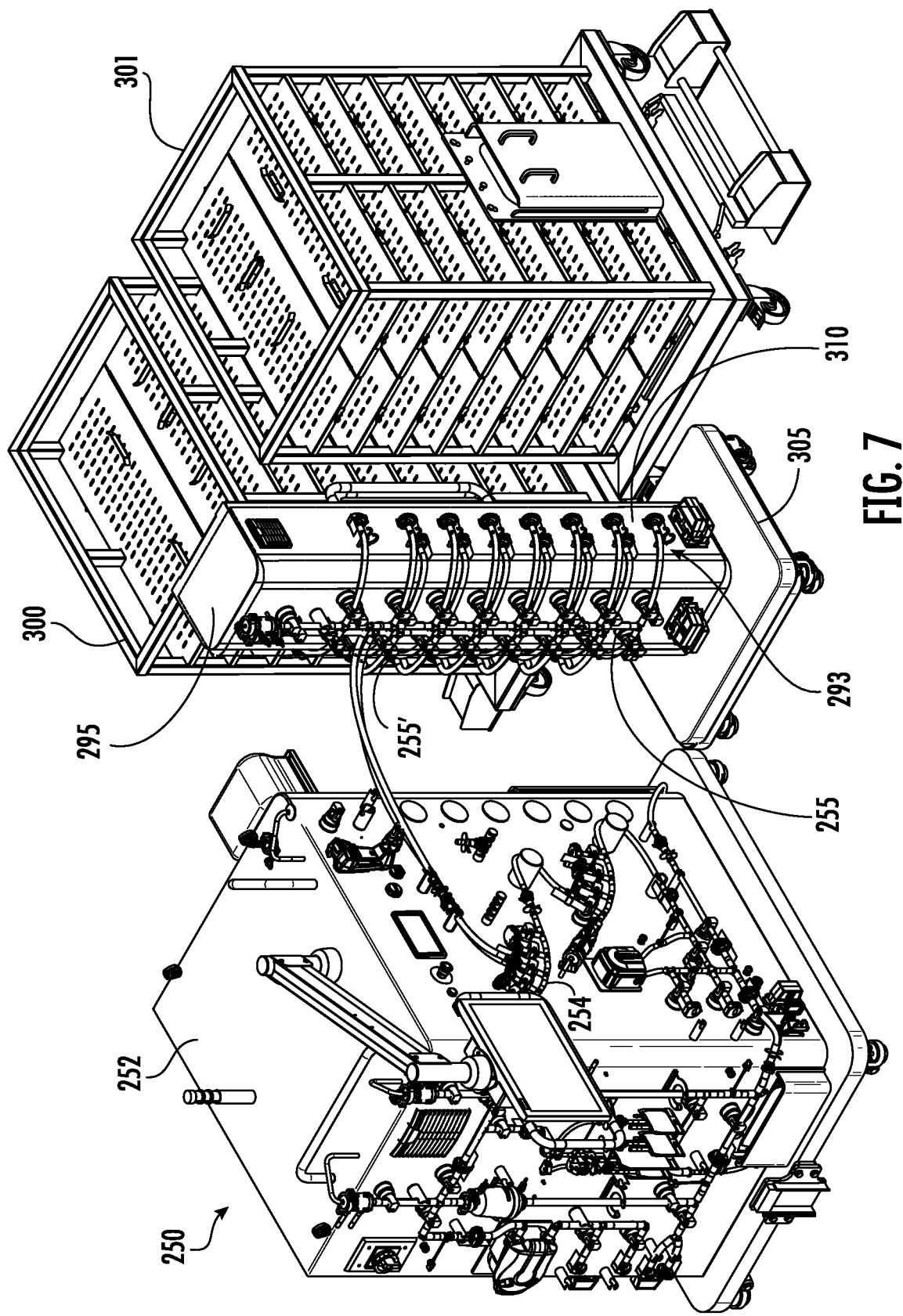
FIG. 7 is a perspective view of another embodiment of a fluid distribution system constructed in accordance with principles of the present disclosure, including a distributor skid and an embodiment of a distribution tower having a single use filler manifold of the fluid distribution system mounted thereto, and a perspective view of another embodiment of a workstation configured to hold a plurality of single use containers for receiving aliquoted portions of fluid from the fluid distribution system.
Figure 8:
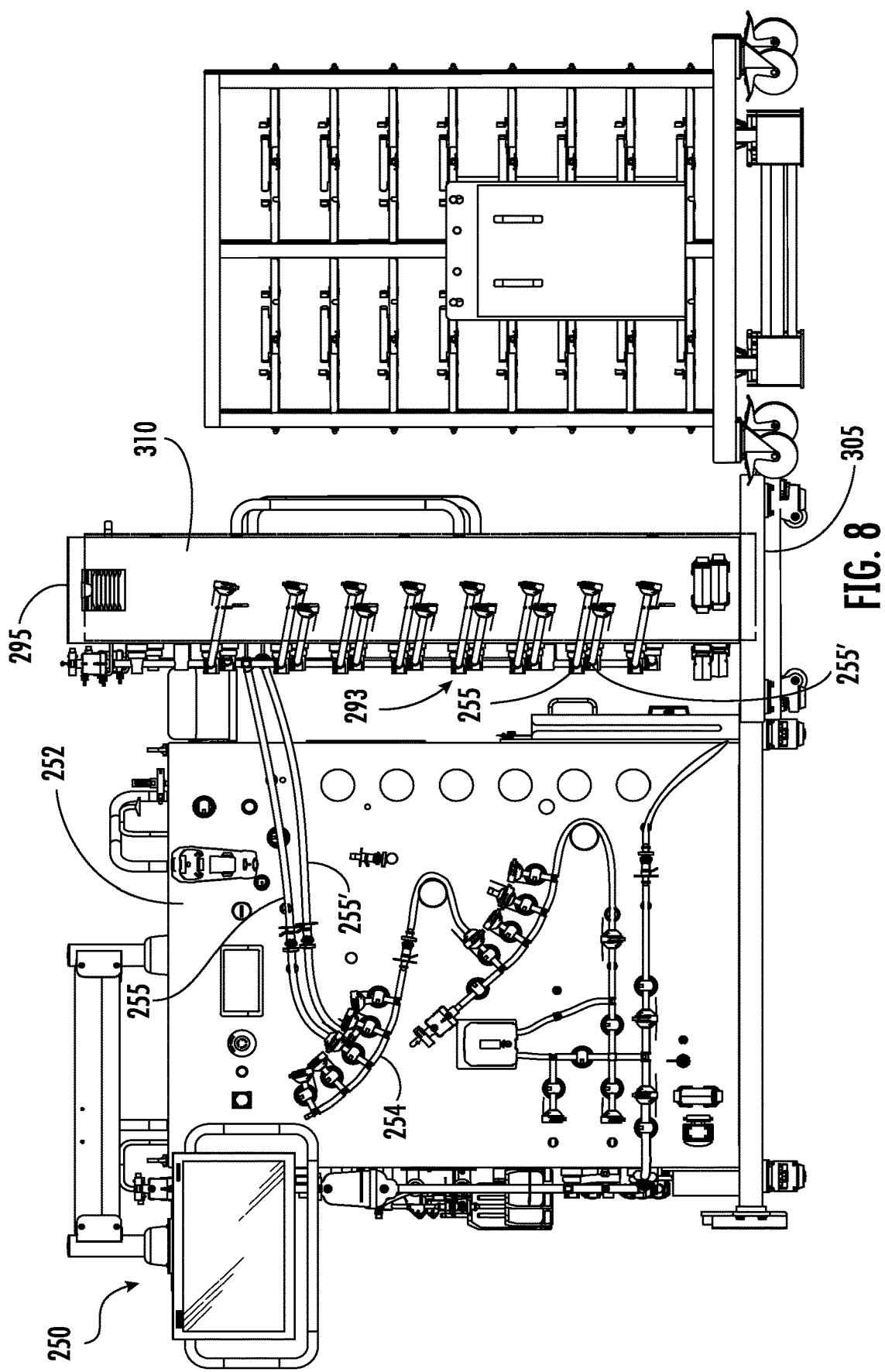
FIG. 8 is an elevational view of the distributor skid, the distribution tower, and the workstation of FIG. 7.

The workstation 100' illustrated in FIGS. 5 and 6 includes a trolley 140, a frame structure 143', and a weigh scale 145. The frame structure 143' is mounted to the trolley 140 and is configured to support one or more biocontainer totes. The frame structure 143' includes an upright structure configured to retain the tote in place and to form a pair of handle portions 152 suitable for gripping when moving the workstation 100' over the surface upon which the wheels of the trolley 140 rest. The workstation 100' comprises a workstation configured to hold fluid in at least one single use tote that the fluid distribution system 50' aliquoted from a larger supply. The workstation 100' of FIG. 5 can be similar in other respects to the workstation 100 of FIG. 3.

Referring to FIGS. 7-10, in embodiments, a fluid distribution system 250 constructed according to principles of the present disclosure includes at least one single use filler manifold 255 and at least one filler valve arrangement 293 mounted to a distribution tower 295 separate from the distributor skid 252. The illustrated distribution tower 295 comprises a trolley 305 and a filling tower 310. The filling tower 310 extends from the trolley 305. In the embodiment shown in FIGS. 7 and 8, two of the set of single use filler manifolds 255, 255' are mounted to the filling tower of the distribution tower. In embodiments, the filler valve arrangement 293 is mounted to the tower 310 and can be associated with one of the single use filler manifolds 255 mounted to the filling tower 310 such that the valves of the filler valve arrangement 293 are respectively associated with each one of the filler manifold outlets. The filler manifold outlets of this single use filler manifold 255 can be placed in respective fluid communication with a corresponding plurality of single use containers that can be supported by the workstations 300, 301.

In embodiments, after the first one of the single use filler manifolds 255 mounted to the filling tower 310 is used in a filling operation, the other of the single use filler manifolds 255' mounted to the filling tower 310 can be associated with the filler valve arrangement 293 mounted to the filling tower 310 and another of the intermediary distributor manifold outlets of the intermediary single use distributor manifold 254. The other of the single use filler manifolds 255' mounted to the filling tower 310 can then be used in a second filling operation with a another set of single use containers.

Figure 9:
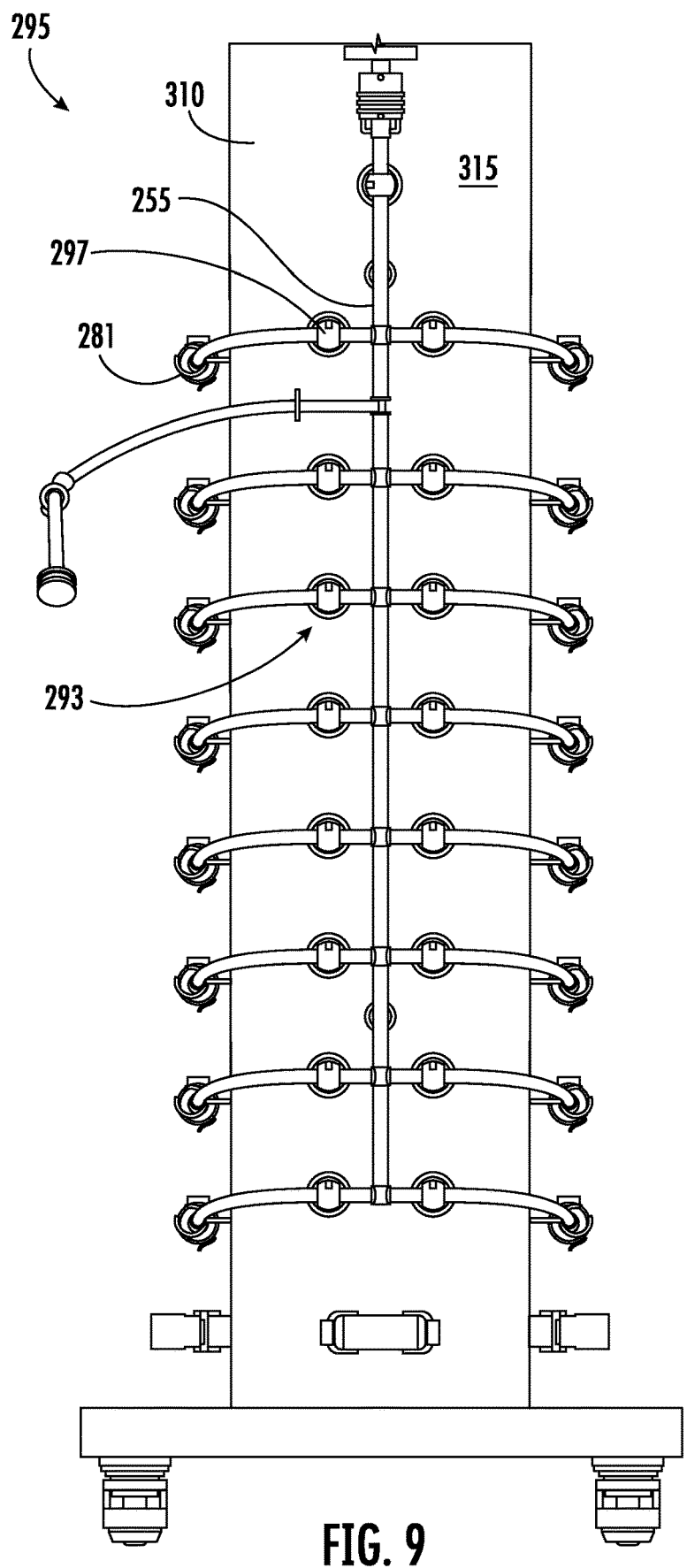
FIG. 9 is another elevational view of the distribution tower of FIG. 7.
Figure 10:
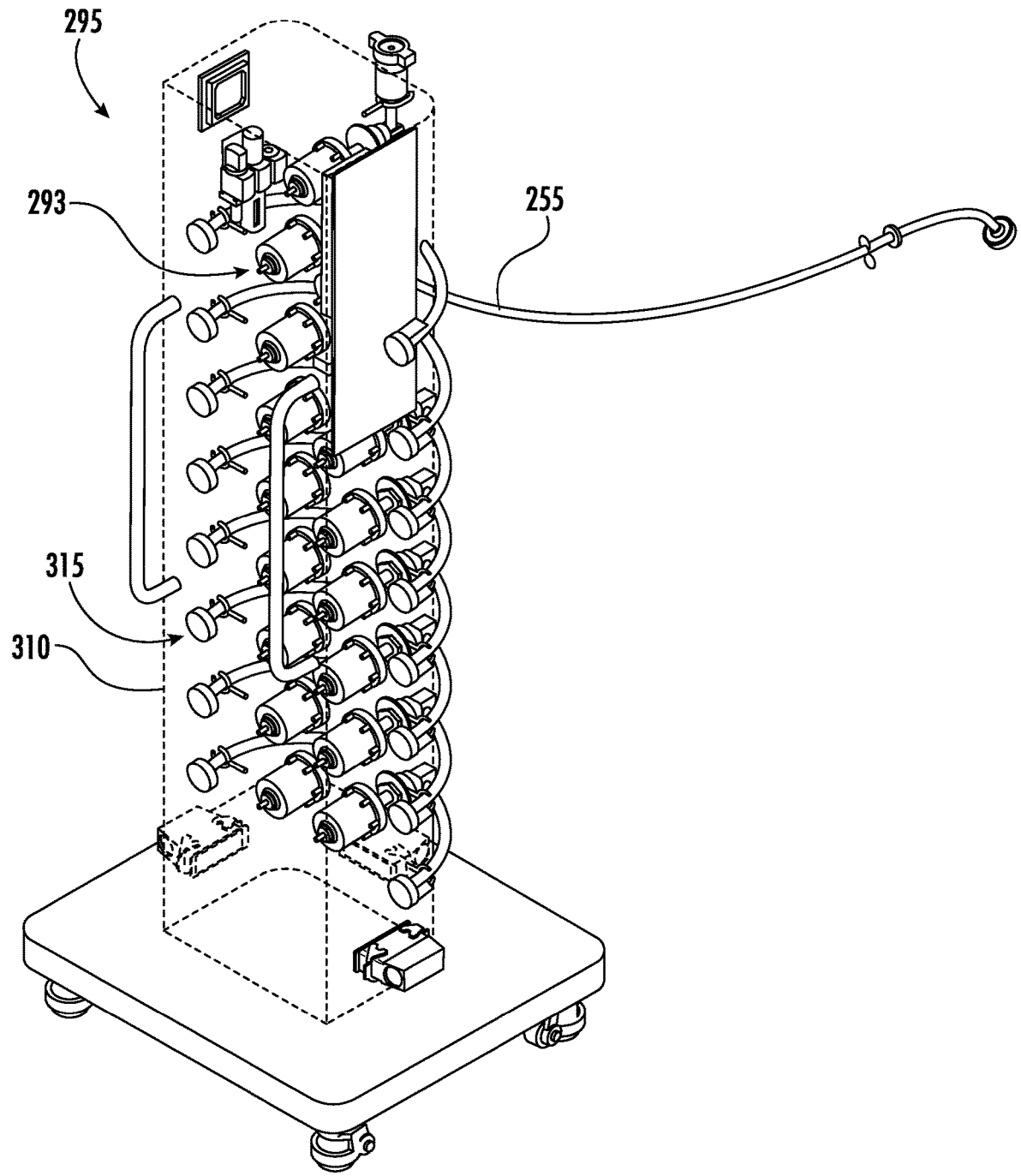
FIG. 10 is a perspective view of the distribution tower of FIG. 7, shown with a cabinet in broken lines for illustrative purposes.

Referring to FIGS. 9 and 10, the filling tower 310 of the distribution tower 295 is shown with a filler valve arrangement 293 and one single use filler manifold 255 mounted thereto. The filling tower 310 includes an enclosure 315 that can support the plurality of valves comprising the filler valve arrangement 293 such that the clamping portions of the valves extends from an exterior surface of the enclosure 315. The clamping portions 297 can be associated with a respective one of the filler manifold outlets 281 as shown in FIG. 9 (only one of which being indicated).

Figure 11:
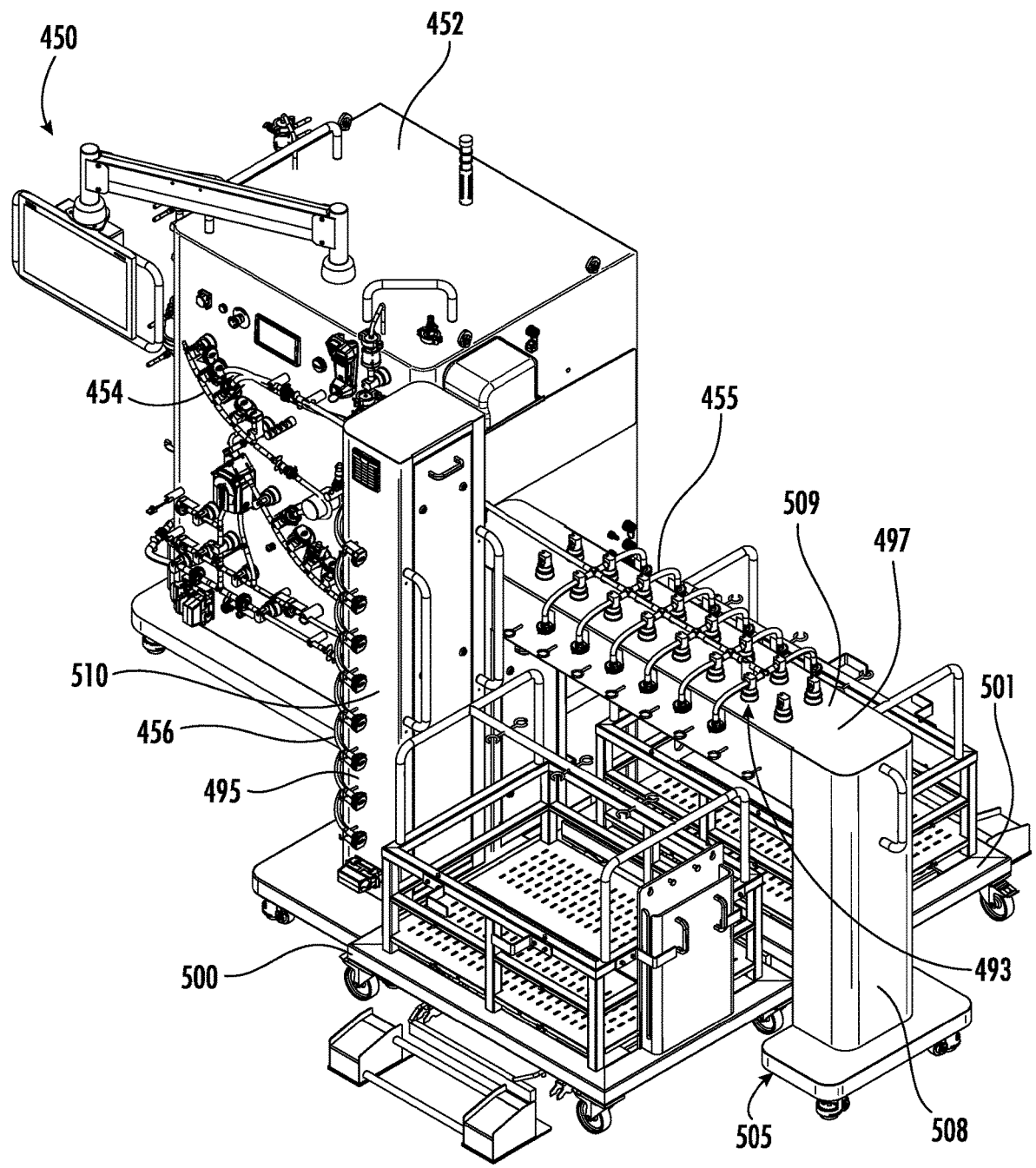
FIG. 11 is a perspective view of another embodiment of a fluid distribution system constructed in accordance with principles of the present disclosure, including a distributor skid, the distribution tower of FIG. 7, and another embodiment of a distribution tower having a single use filler manifold of the fluid distribution system mounted thereto; and a perspective view of another embodiment of a workstation configured to hold a plurality of single use containers for receiving aliquoted portions of fluid from the fluid distribution system.
Figure 12:
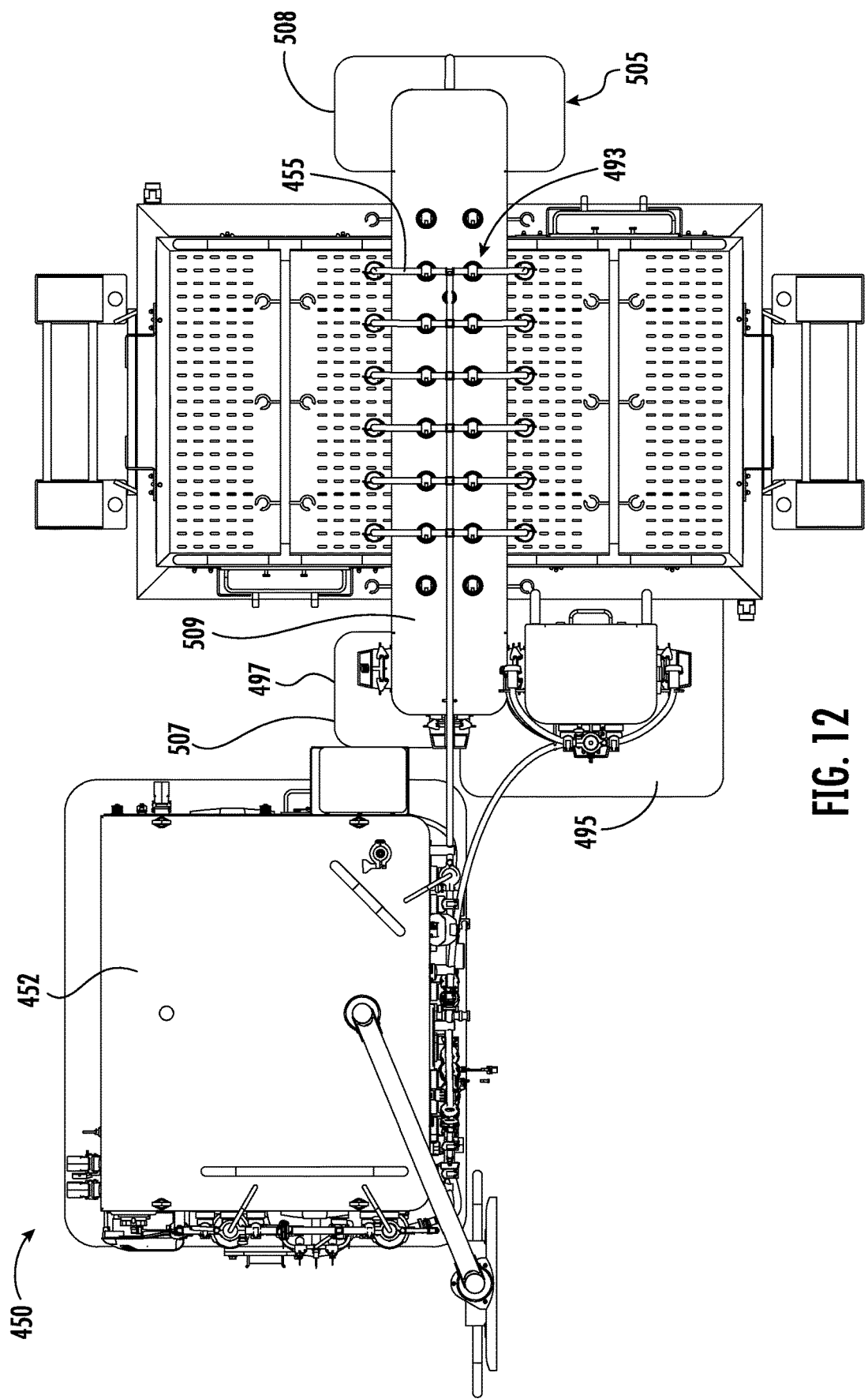
FIG. 12 is a top plan view of the distributor skid, the distribution towers, and the workstation of FIG. 11.

Referring to FIGS. 11 and 12, in embodiments, an embodiment of a fluid distribution system 450 constructed according to principles of the present disclosure includes at least one single use filler manifold 455 and at least one filler valve arrangement 493 mounted to a distribution tower 497 separate from the distributor skid 452. In the embodiment illustrated in FIGS. 11 and 12, a pair of distribution towers 495, 497 are provided. In embodiments, the fluid distribution system 450 includes multiple distribution towers configured to support multiple, different single use containers filled via the fluid distribution system.

In the illustrated embodiment, one distribution tower 495 is similar in construction to the distribution tower 295 of FIGS. 7-10. The other distribution tower 497 comprises a gantry 505 including first and second uprights 507, 508 and a beam 509 extending between upper ends of the first and second uprights 507, 508. Each upright 507, 508 includes a trolley at its base configured to help the mobility of the gantry 505. One of the set of single use filler manifolds 455 and the filler valve arrangement 493 are mounted to the beam.

Referring to FIG. 11, in embodiments, the filler manifold inlet of this single use filler manifold can be placed in fluid communication with one of the intermediary distributor manifold outlets of the single use intermediary distributor manifold 454 mounted to the distributor skid 452. The filler manifold outlets of this single use filler manifold 455 can be placed in respective fluid communication with a corresponding plurality of single use containers that can be supported by the workstations 500, 501.

In embodiments, the filler manifold inlet of the single use filler manifold 456 mounted to the filling tower 510 can be placed in fluid communication with another of the intermediary distributor manifold outlets of the single use intermediary distributor manifold 454 mounted to the distributor skid 452. The filler manifold outlets of this single use filler manifold 456 can be placed in respective fluid communication with another set of single use containers that can be supported by the workstations 500, 501 or other, differently-configured workstations, such as those shown in FIG. 7, for example.

In other embodiments, a fluid distribution system constructed according to principles of the present disclosure can include different equipment configured to hold the supply of fluid for delivery to the manifolds for distributed, scaled dispensing in a plurality of single use containers. For example, in other embodiments, a fluid distribution system constructed according to principles of the present disclosure can include at least one tower configured to hold one or more totes filled with a fluid for use with the fluid distribution system. In other embodiments, a fluid distribution system constructed according to principles of the present disclosure can include one or more tanks filled with a fluid for use in the system.

In other embodiments of a fluid distribution system constructed in accordance with principles of the present disclosure, the fluid distribution system construction can take alternatives forms. For example, in embodiments, the distribution towers can be replaced by totes. In other embodiments, the fluid distribution system can be scaled for larger volumes or decreased for laboratory usage. In embodiments, the fluid distribution system can include single use manifolds constructed from rigid plastic construction. In embodiments, a fluid distribution system constructed according to principles of the present disclosure can be used to process a variety of liquids to meet the requirements of a desired application.

In embodiments of a method of using a fluid distribution system following principles of the present disclosure, a fluid distribution system constructed according to principles of the present disclosure is used to deliver portions of fluid to a series of single use containers as discussed herein. In embodiments, a method of using a fluid distribution system following principles of the present disclosure can be used with any embodiment of a fluid distribution system according to principles discussed herein, which can include an embodiment of a distributor skid having at least one single use distributor manifold according to principles of the present disclosure.

In one embodiment, a method of aseptically distributing fluid includes feeding a fluid into a distributor manifold inlet of a single use distributor manifold. A first supply of the fluid is discharged from a first one of a plurality of distributor manifold outlets of the single use distributor manifold to a filler manifold inlet of a first single use filler manifold via a first aseptic fluid pathway. Portions of the first supply of the fluid are respectively discharged from a plurality of filler manifold outlets of the first single use filler manifold to a respective one of a first set of single use containers respectively aseptically fluidly connected to the plurality of filler manifold outlets of the first single use filler manifold. After the portions of the first supply of the fluid are discharged, the first single use filler manifold is disconnected from the single use distributor manifold.

A second supply of the fluid is discharged from a second one of the plurality of distributor manifold outlets of the single use distributor manifold to a filler manifold inlet of a second single use filler manifold via a second aseptic fluid pathway. Portions of the second supply of the fluid are respectively discharged from a plurality of filler manifold outlets of the second single use filler manifold to a respective one of a second set of single use containers respectively aseptically fluidly connected to the plurality of filler manifold outlets of the second single use filler manifold.

In embodiments, the method further includes sequentially discharging an additional supply of the fluid from each other distributor manifold outlet port of the single use distributor manifold to a filler manifold inlet of a respective other single use filler manifold via a respective separate aseptic fluid pathway. Portions of the additional supply of the fluid are respectively discharged from a plurality of filler manifold outlets of each respective other single use filler manifold to a respective one of an additional set of single use containers respectively aseptically fluidly connected to the plurality of filler manifold outlets of each respective other single use filler manifold. After respectively discharging the portions of the additional supply of the fluid, each respective other single use filler manifold is disconnected from the single use distributor manifold.

In embodiments, the method further includes installing the single use distributor manifold in a filling skid before feeding the fluid into the distributor manifold inlet of the single use distributor manifold. The single use distributor manifold is removed from the filling skid after sequentially discharging the additional supply of the fluid from each other distributor manifold outlet port of the single use distributor manifold.

In embodiments, the single use distributor manifold comprises a first single use distributor manifold. In embodiments, the first supply of the fluid is discharged from the first one of a plurality of distributor manifold outlets of the single use distributor manifold by feeding the first supply of the fluid into a distributor manifold inlet of a second single use distributor manifold. The second single use distributor manifold in the first aseptic fluid pathway is interposed between the first one of the plurality of distributor manifold outlets of the first single use distributor manifold and the filler manifold inlet of the first single use filler manifold, and the first supply of the fluid is discharged from a first one of a plurality of distributor manifold outlets of the second single use distributor manifold to the filler manifold inlet of the first single use filler manifold via the first aseptic fluid pathway.

In another embodiment, a method of aseptically distributing fluid includes feeding a first supply of fluid into a distributor manifold inlet of a first single use distributor manifold. A first supply of fluid is discharged from a first one of a plurality of distributor manifold outlets of the first single use distributor manifold to a distributor manifold inlet of a second single use distributor manifold via a first aseptic fluid pathway. The first supply of fluid is discharged from a first one of a plurality of distributor manifold outlets of the second single use distributor manifold to a filler manifold inlet of a first single use filler manifold via a second aseptic fluid pathway. Portions of the first supply of fluid are respectively discharged from a plurality of filler manifold outlets of the first single use filler manifold to a respective one of a first set of single use containers respectively aseptically fluidly connected to the plurality of filler manifold outlets of the first single use filler manifold.

After the portions of the first supply of fluid are discharged, the first single use filler manifold is disconnected from the second single use distributor manifold, and a second single use filler manifold is connected to a second one of the plurality of distributor manifold outlets of the second single use distributor manifold via a third aseptic fluid pathway. A second supply of fluid is fed into the distributor manifold inlet of the first single use distributor manifold. The second supply of fluid is discharged from the first one of the plurality of distributor manifold outlets of the first single use distributor manifold to the distributor manifold inlet of the second single use distributor manifold via the first aseptic fluid pathway. The second supply of fluid is discharged from a second one of the plurality of distributor manifold outlets of the second single use distributor manifold to a filler manifold inlet of the second single use filler manifold via the third aseptic fluid pathway. Portions of the second supply of fluid are respectively discharged from a plurality of filler manifold outlets of the second single use filler manifold to a respective one of a second set of single use containers respectively aseptically fluidly connected to the plurality of filler manifold outlets of the second single use filler manifold.

In embodiments, the method further includes sequentially discharging an additional supply of fluid from each other distributor manifold outlet port of the second single use distributor manifold to a filler manifold inlet of a respective other single use filler manifold via a respective separate aseptic fluid pathway. Portions of the additional supply of fluid are respectively discharged from a plurality of filler manifold outlets of each respective other single use filler manifold to a respective one of an additional set of single use containers respectively aseptically fluidly connected to the plurality of filler manifold outlets of each respective other single use filler manifold.

In embodiments, the method further includes, after respectively discharging the portions of the additional supply of fluid, disconnecting each respective other single use filler manifold from the second single use distributor manifold. In embodiments, the method further includes, after sequentially discharging the additional supply of fluid from each other distributor manifold outlet port of the second single use distributor manifold, disconnecting the second single use distributor manifold and connecting a second one of the plurality of distributor manifold outlets of the first single use distributor manifold to a distributor manifold inlet of a third single use distributor manifold via a fourth aseptic fluid pathway.

In embodiments, the method further includes feeding a third supply of fluid into the distributor manifold inlet of the first single use distributor manifold. The third supply of fluid is discharged from the second one of the plurality of distributor manifold outlets of the first single use distributor manifold to the distributor manifold inlet of the third single use distributor manifold via the fourth aseptic fluid pathway. The third supply of fluid is discharged from a first one of a plurality of distributor manifold outlets of the third single use distributor manifold to a filler manifold inlet of a third single use filler manifold via a fifth aseptic fluid pathway. Portions of the third supply of fluid are respectively discharged from a plurality of filler manifold outlets of the third single use filler manifold to a respective one of a third set of single use containers respectively aseptically fluidly connected to the plurality of filler manifold outlets of the third single use filler manifold.

In embodiments, the method further includes sequentially discharging an additional supply of fluid from each other distributor manifold outlet port of the third single use distributor manifold to a filler manifold inlet of a respective other single use filler manifold via a respective separate aseptic fluid pathway. Portions of the additional supply of fluid are respectively discharged from a plurality of filler manifold outlets of each respective other single use filler manifold to a respective one of an additional set of single use containers respectively aseptically fluidly connected to the plurality of filler manifold outlets of each respective other single use filler manifold.

In embodiments, the method further includes sequentially discharging a respective one of an additional set of supplies of fluid from each other distributor manifold outlet port of the first single use distributor manifold to a set of intermediary single use distributor manifolds.

In another embodiment of a method of aseptically distributing fluid following principles of the present disclosure, the method includes sequentially discharging a supply of a fluid from a different one of a plurality of distributor manifold outlets of a single use distributor manifold, each of the distributor manifold outlets being in fluid communication with a filler manifold inlet of a respective one of a corresponding plurality of single use filler manifolds via a corresponding aseptic fluid conduit, wherein sequentially discharging the supplies of the fluid is performed by operating a valve arrangement to sequence through a series of different conditions including, for each distributor manifold outlet port, the distributor manifold outlet port is opened and the other distributor manifold outlets are occluded.

In embodiments, for each single use filler manifold, a portion of the supply of the fluid received from the one of the distributor manifold outlets in fluid communication therewith is discharged from each of a plurality of filler manifold outlets to one of a corresponding set of single use containers respectively aseptically fluidly connected thereto. In embodiments, sequentially discharging the supplies of the fluid is performed by operating a valve arrangement to sequentially open each one of the aseptic fluid conduits with the other aseptic fluid conduits are occluded.

Figure 13:
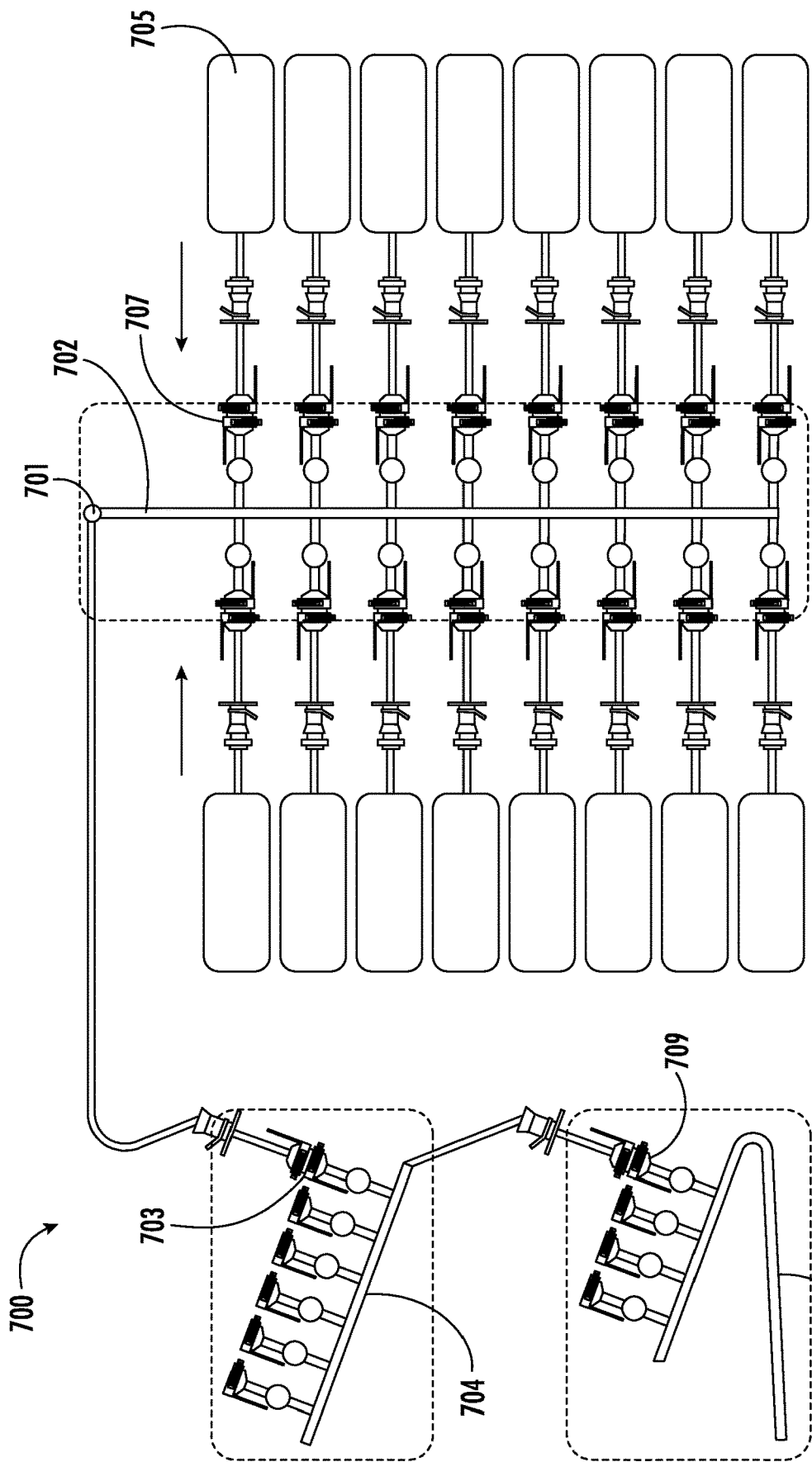
Figure 15:
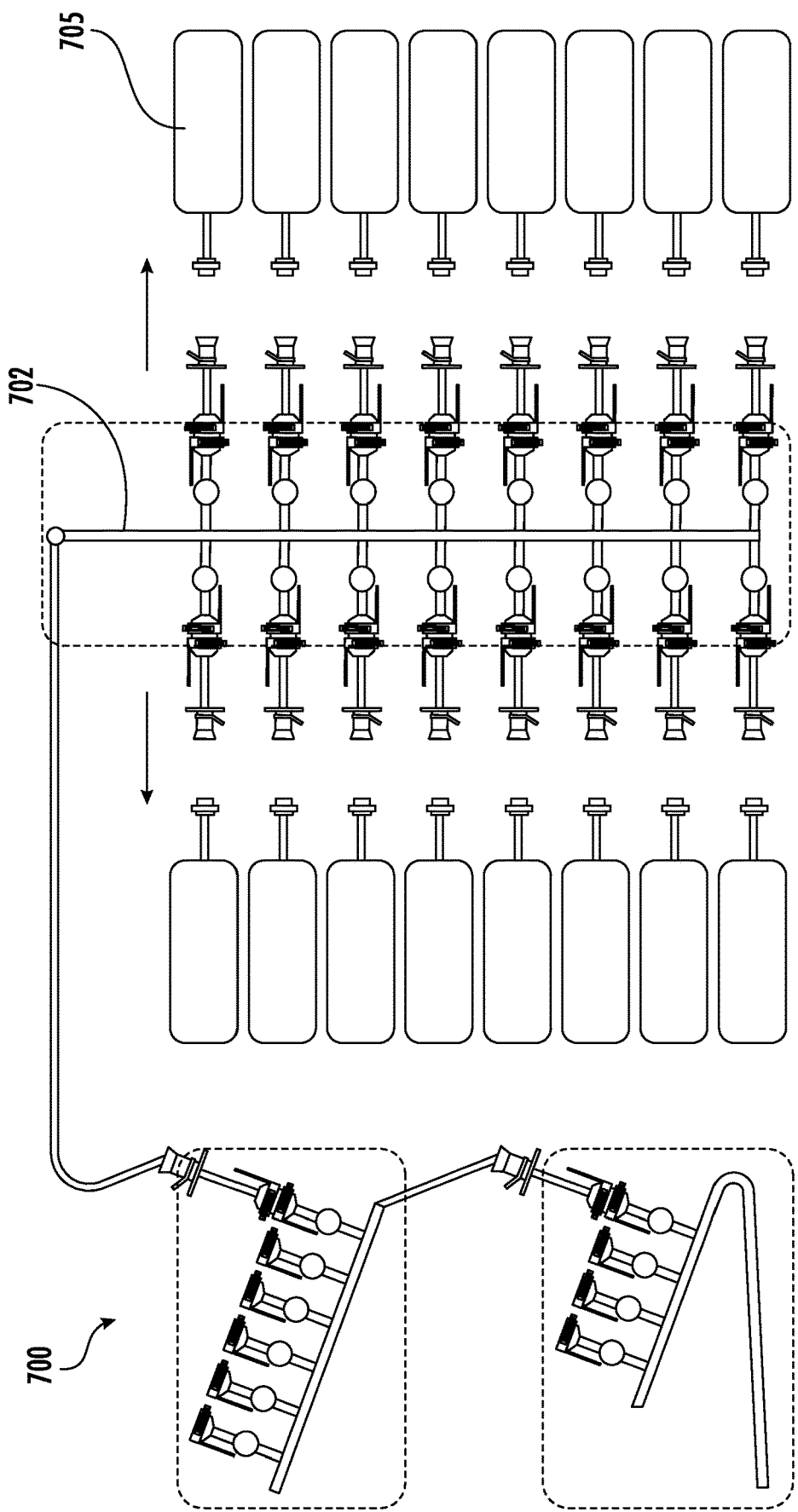
Figure 16:
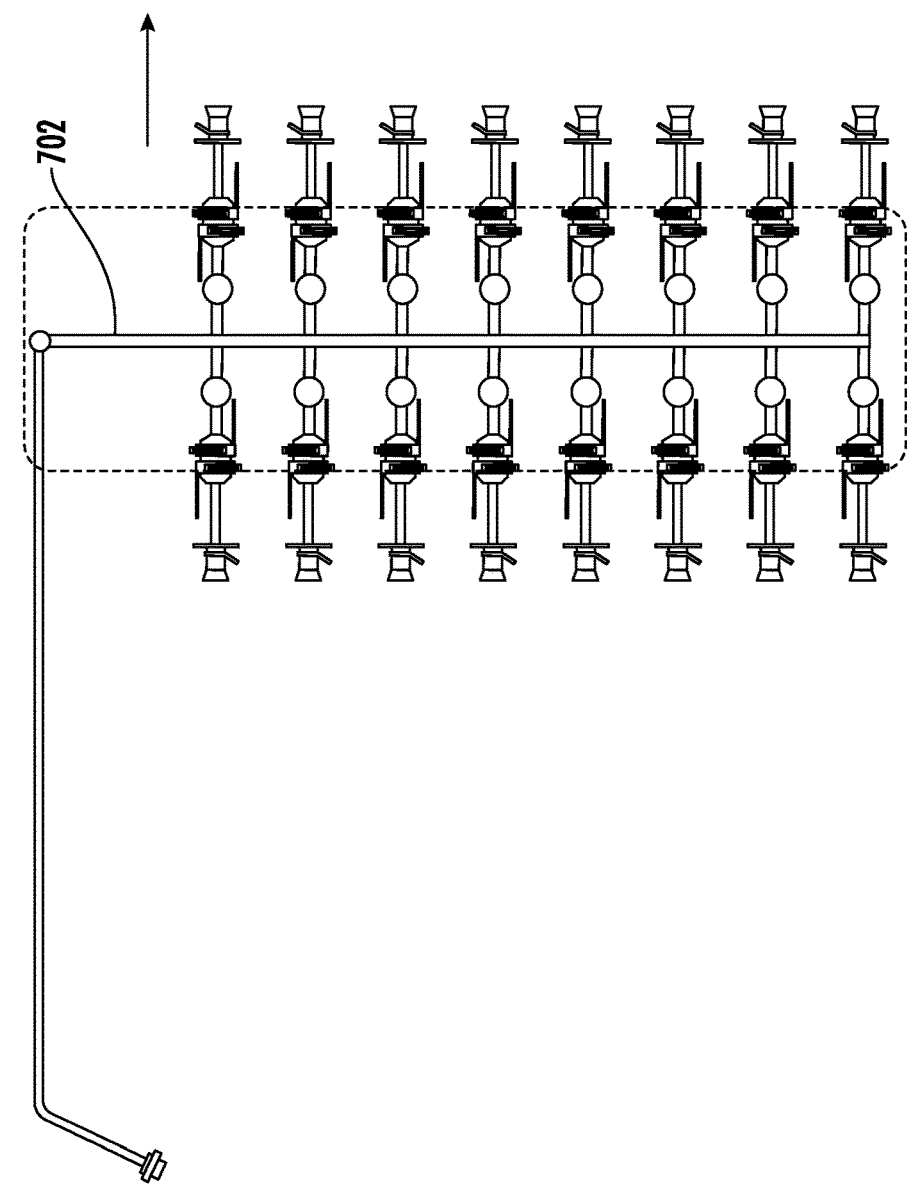

Referring to FIGS. 13-32, a series of filling sequences is shown. FIGS. 13-16 depict a first filling sequence 700. Referring to FIG. 13, the filler manifold inlet 701 of a first one 702 of the set of filler manifolds is connected to the first intermediary distributor manifold outlet 703 of a first intermediary distributor manifold 704. A first set 705 of single use containers can be aseptically connected to the filler manifold outlets 707, respectively, of the first filler manifold 702. Referring to FIG. 14, the first set 705 of single use containers can be filled with fluid passed through a first upstream distributor manifold 708 and the first intermediary distributor manifold 704 which is fluidly connected to the first upstream distributor manifold outlet 709 of the first upstream distributor manifold 708. Referring to FIG. 15, the first set of single use container can be disconnected from the first filler manifold 702. Referring to FIG. 16, after the fluid distribution system is used to distribute fluid to the first set of containers aseptically connected to the outlets of the first single use filler manifold 702, the first single use filler manifold 702 can be disconnected from the first outlet 703 of the intermediary single use distributor manifold 704.

Figure 17:
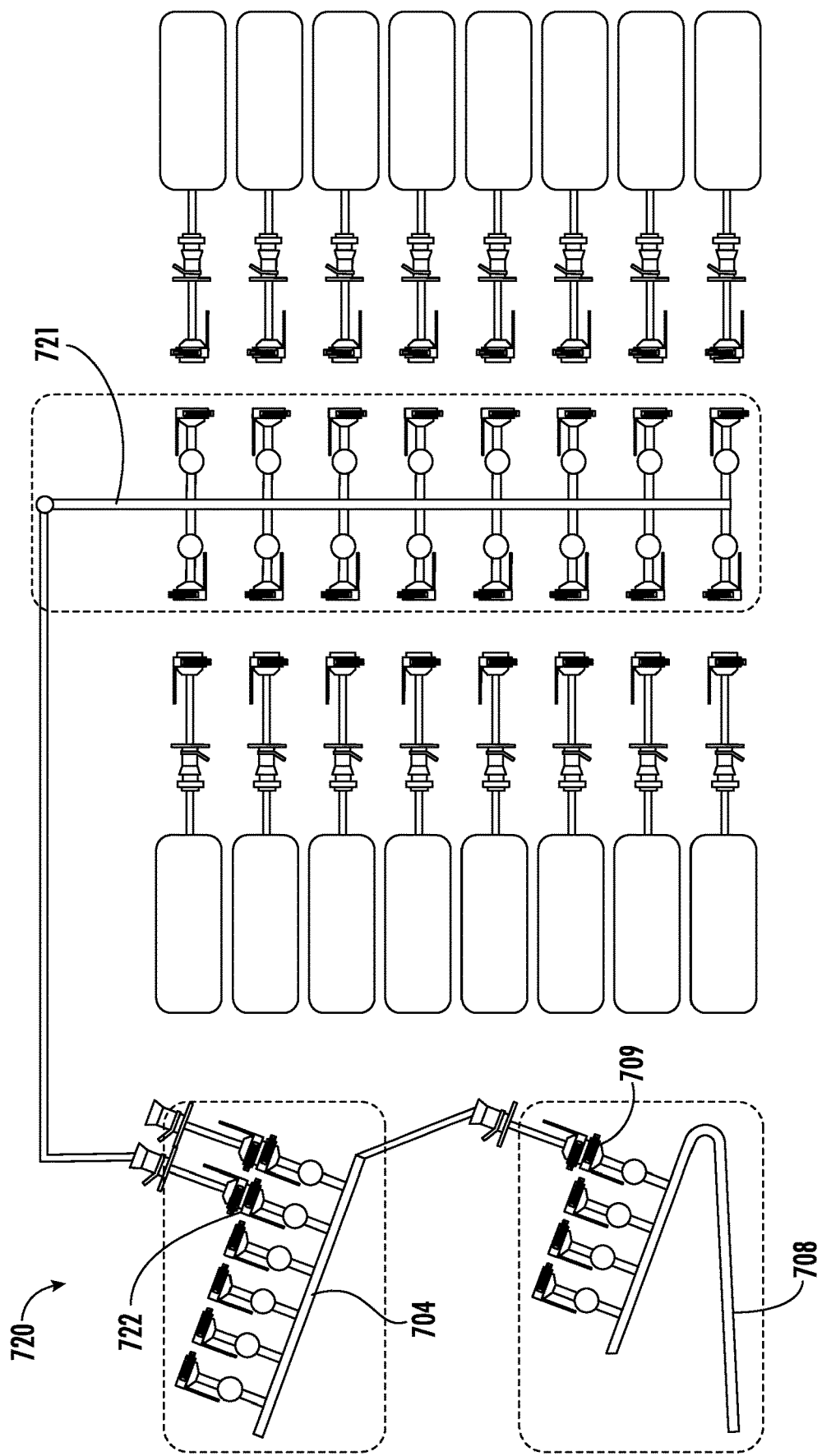
Figure 18:
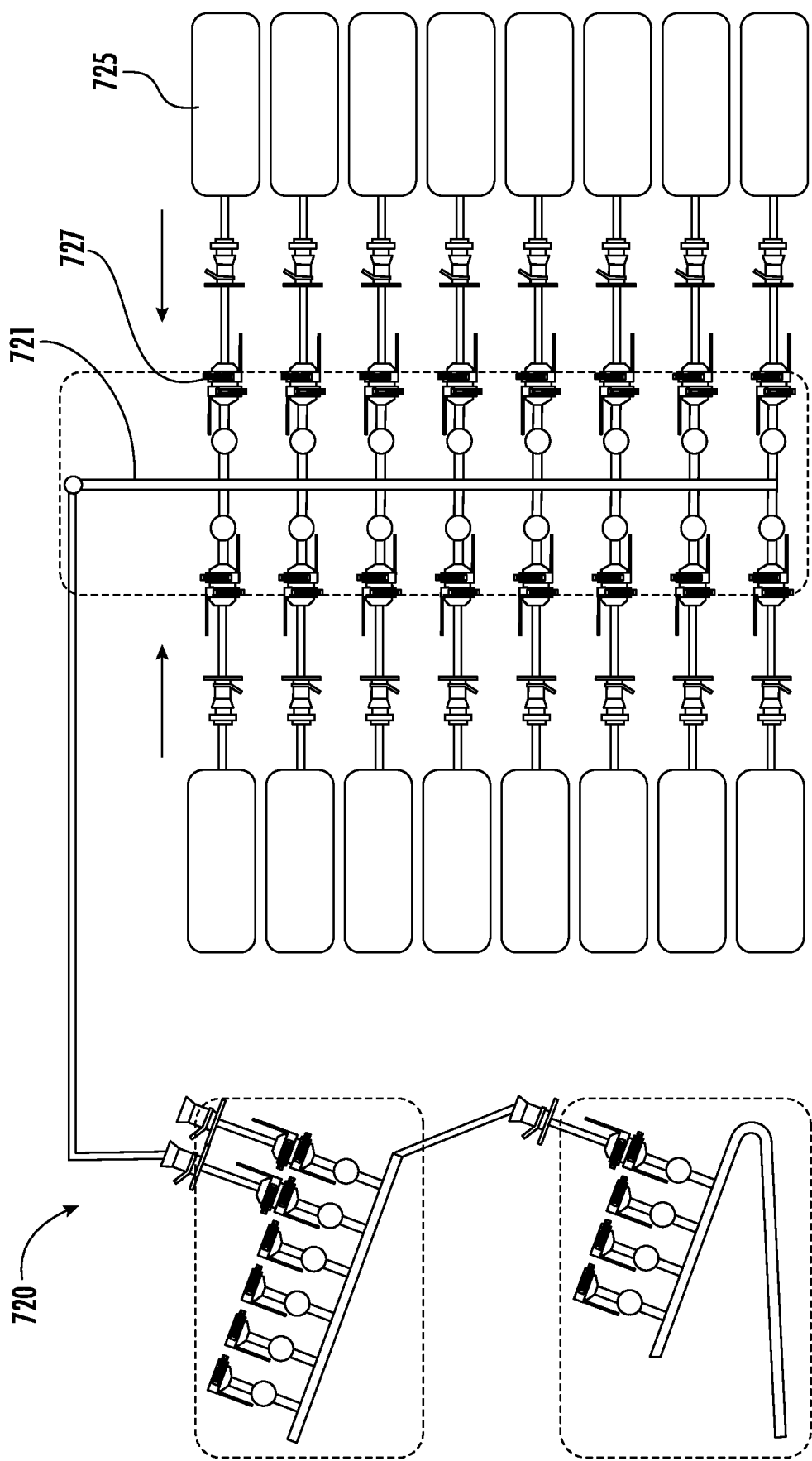
Figure 19:
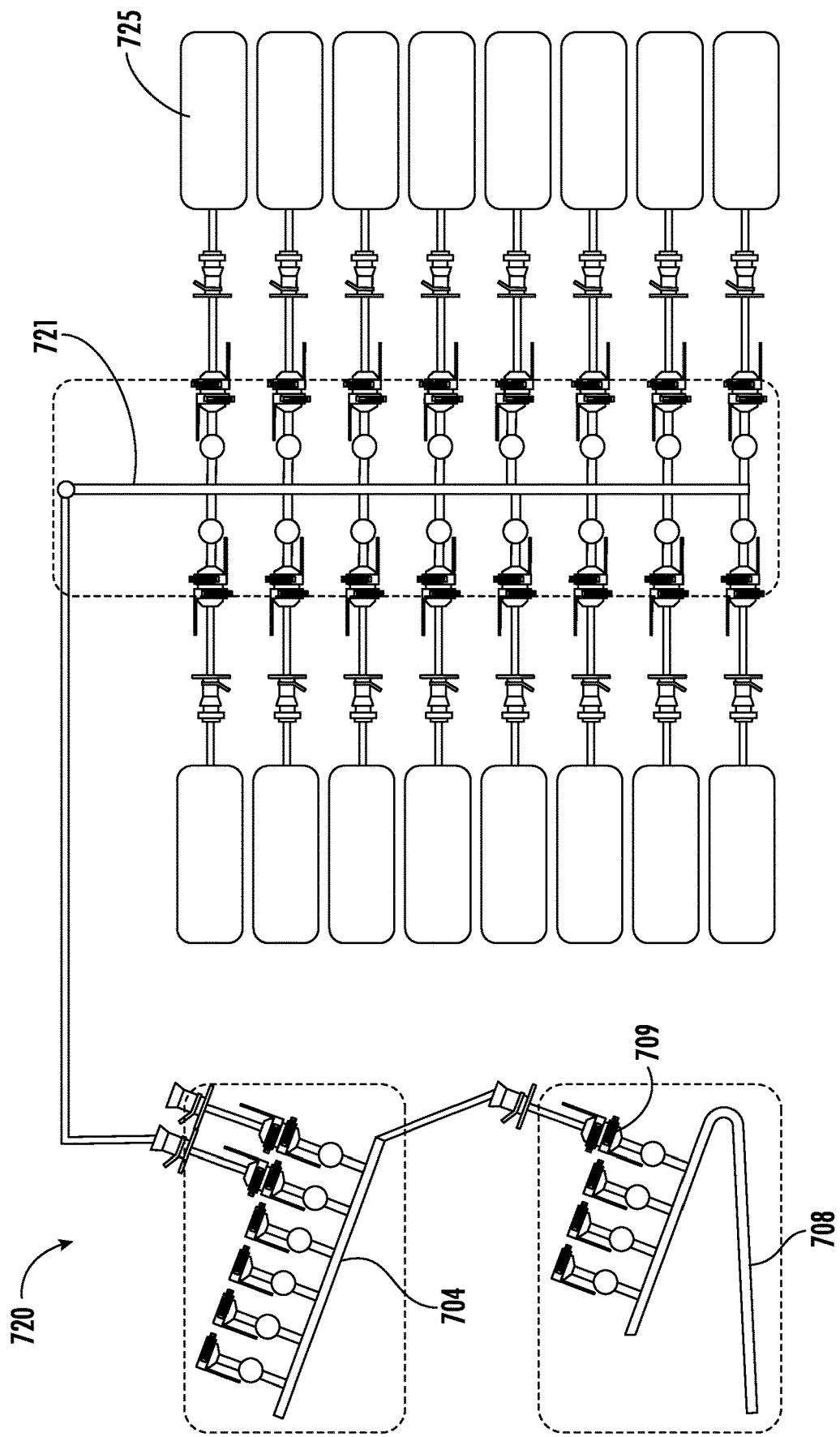
Figure 20:
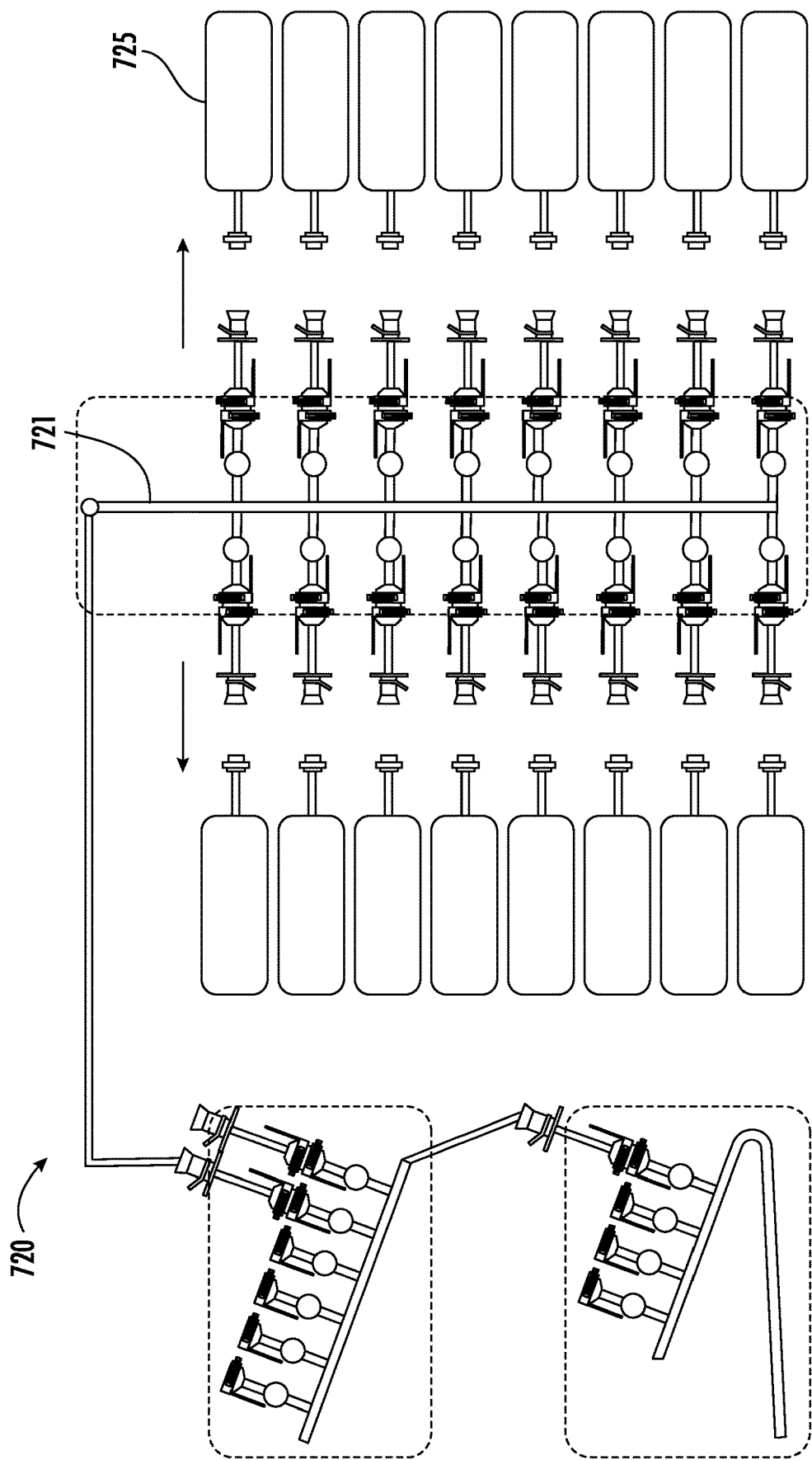
Figure 21:
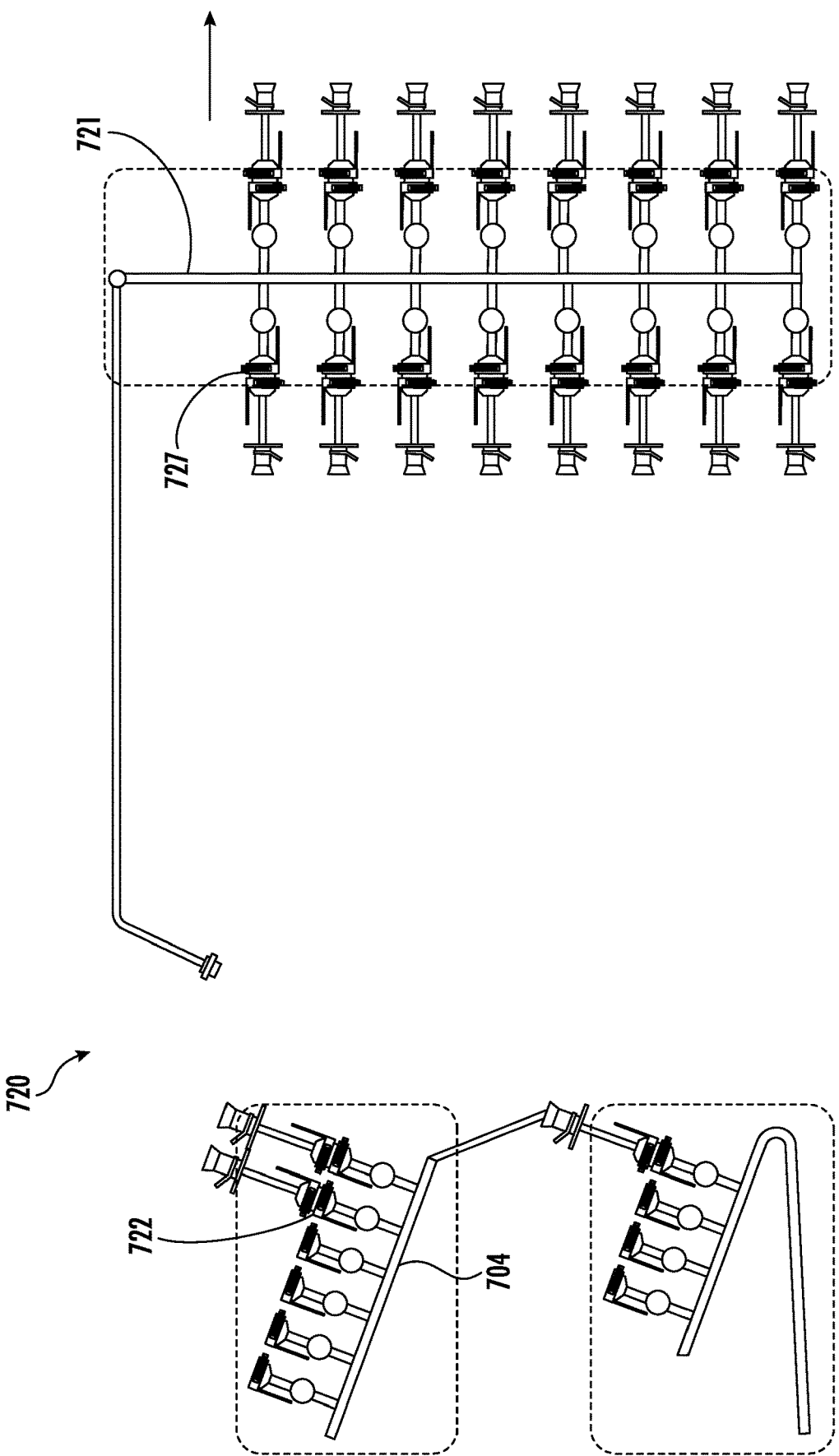
Figure 22:
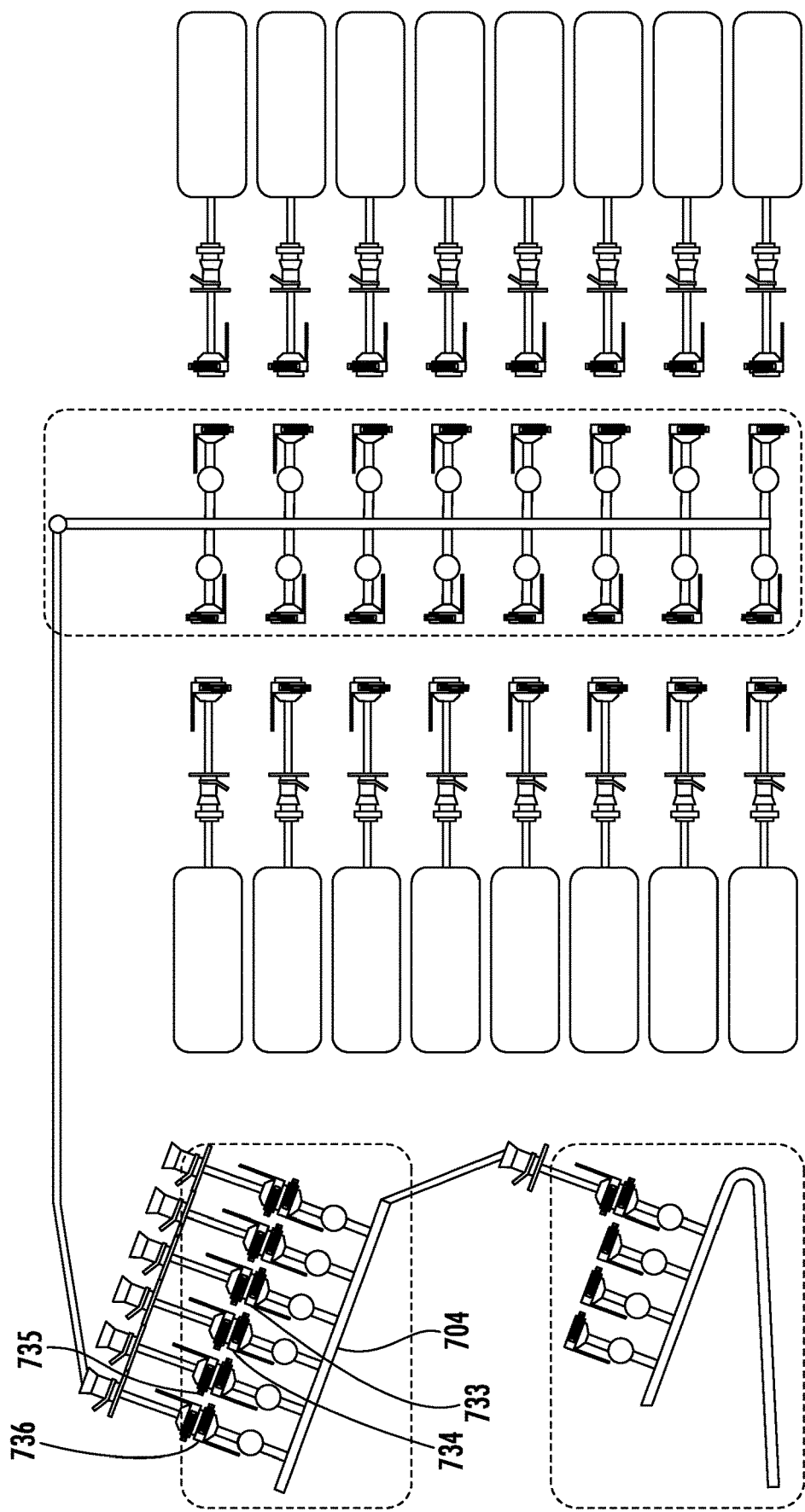

FIGS. 17-21 depict a second filling sequence 720. Referring to FIG. 17, another one 721 of the set of single use filler manifolds can be aseptically connected to the second outlet 722 of the first intermediary single use distributor manifold 704. Referring to FIG. 18, a second set 725 of single use containers can be aseptically connected to the outlets 727 of the second single use filler manifold 721. Referring to FIG. 19, the fluid distribution system can be used to distribute fluid to the second set 725 of containers aseptically connected to the outlets 727 of the second single use filler manifold 721. The second set 721 of single use containers can be filled with fluid passed through the first upstream distributor manifold 708 and the first intermediary distributor manifold 704 which is fluidly connected to the first upstream distributor manifold outlet 709 of the first upstream distributor manifold 708. Referring to FIG. 20, the second set 725 of single use containers can be disconnected from the second filler manifold 721. Referring to FIG. 21, after the fluid distribution system is used to distribute fluid to the second set of containers aseptically connected to the outlets 727 of the second single use filler manifold 721, the second single use filler manifold 721 can be disconnected from the second outlet 722 of the first intermediary single use distributor manifold 704.

Referring to FIGS. 22-26, the filling sequence depicted in FIGS. 17-21 can be repeated for each one of the remaining outlets 733, 734, 735, 736 of the first intermediary single use distributor manifold 704.

Figure 27:
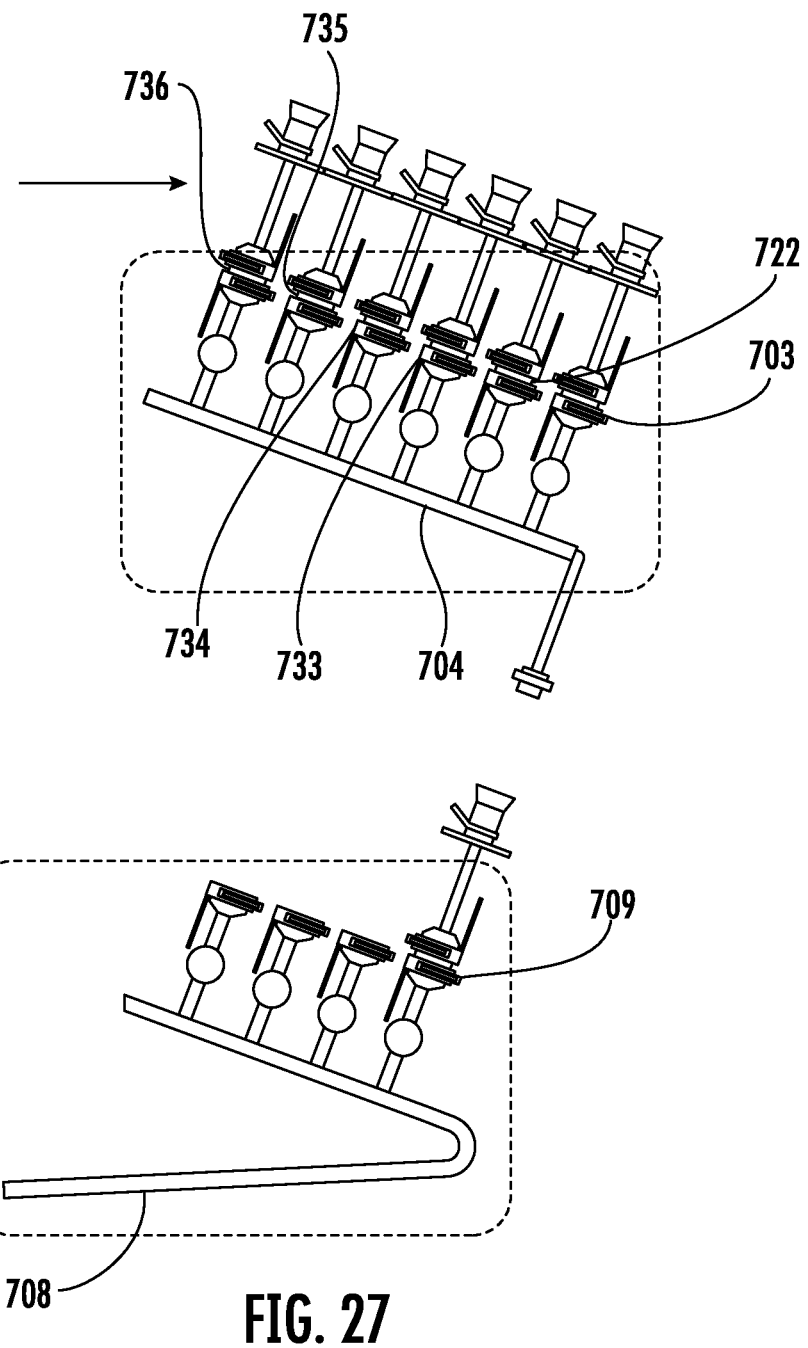
Figure 28:
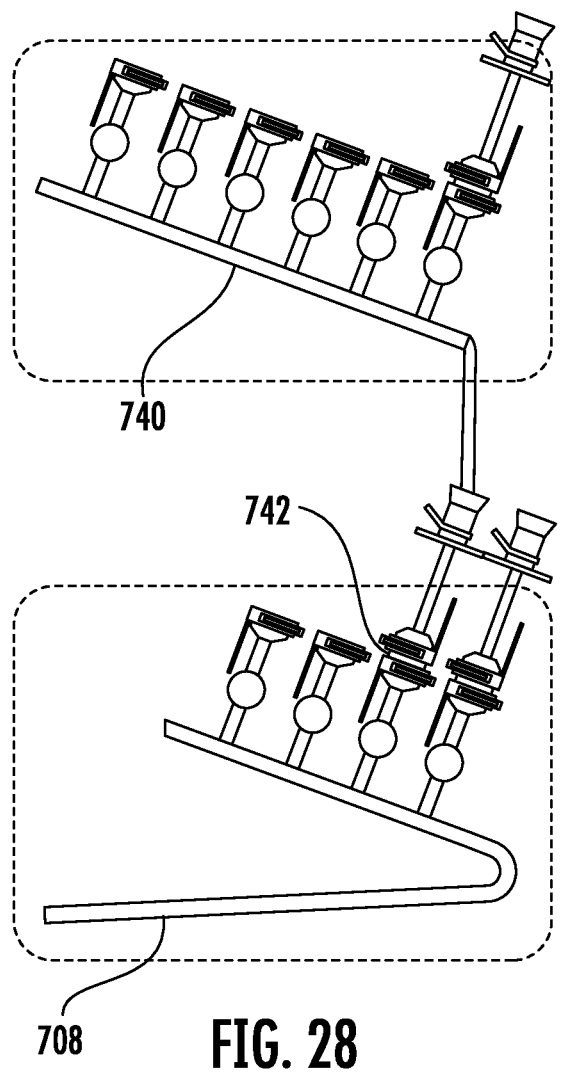
Figure 29:
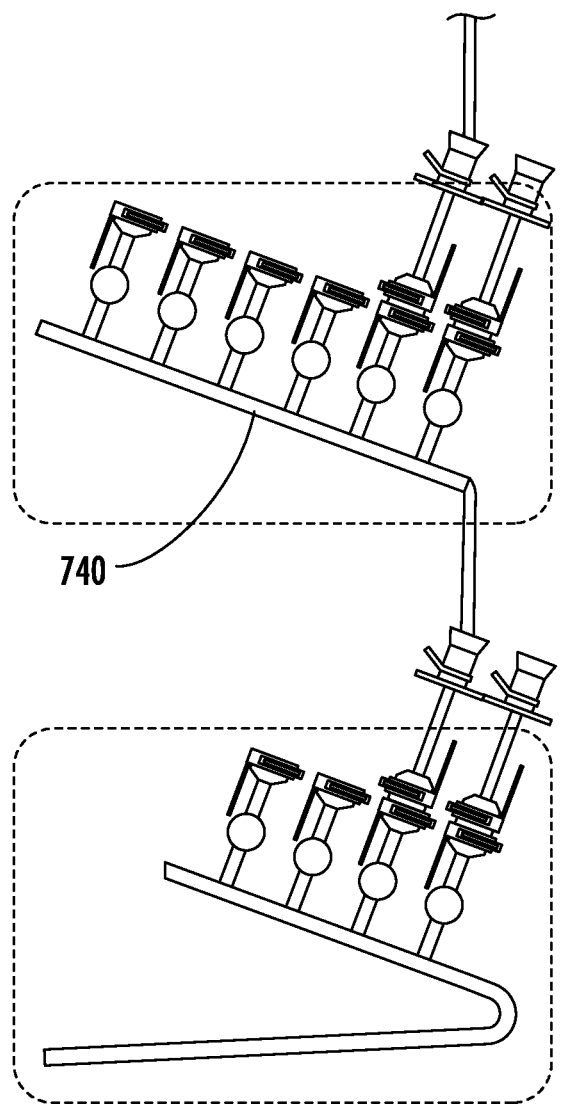
Figure 30:
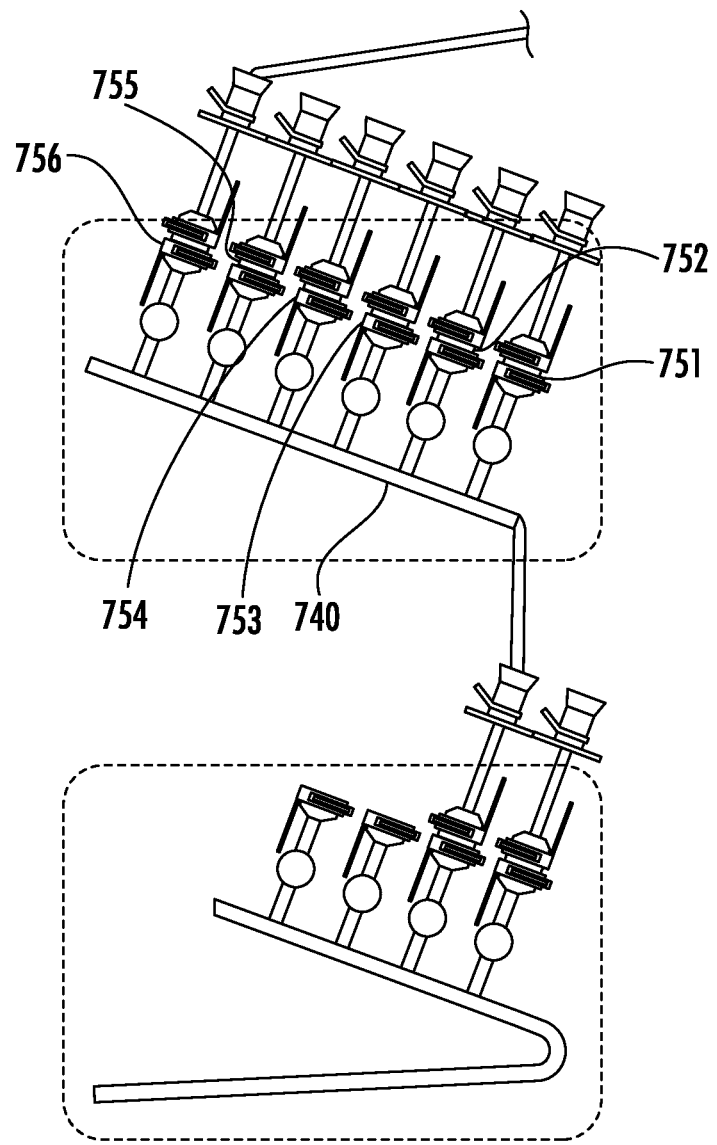
Figure 31:
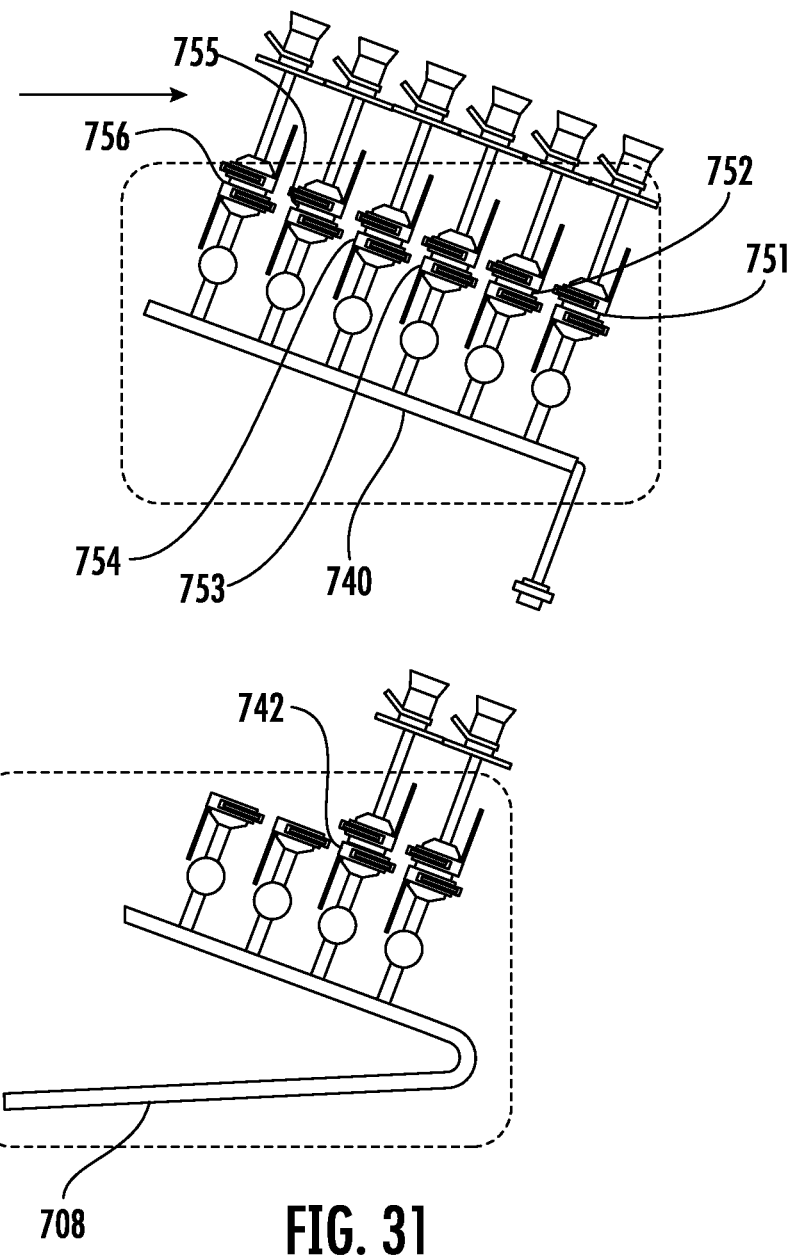

Referring to FIG. 27, after each outlet 703, 722, 733-736 of the first intermediary distributor manifold 704 has been used to perform a filling sequence, the first intermediary distributor manifold 704 can be disconnected from the first outlet 709 of the upstream distributor manifold 708. Referring to FIG. 28, a second one 740 of the set of intermediary distributor manifolds can be aseptically connected to a second outlet 742 of the upstream distributor manifold 708. Referring to FIG. 29, the second intermediary distributor manifold 740 can be used in a manner similar to that described above in connection with the first intermediary distributor manifold. Referring to FIG. 30, the filling sequences depicted in FIGS. 17-21 can be repeated for each one of the outlets 751-756 of the second intermediary single use distributor manifold 740. Referring to FIG. 31, after each outlet 751-756 of the second intermediary distributor manifold 740 has been used to perform a filling sequence, the second intermediary distributor manifold 740 can be disconnected from the second outlet 742 of the upstream distributor manifold 708.

Figure 32:
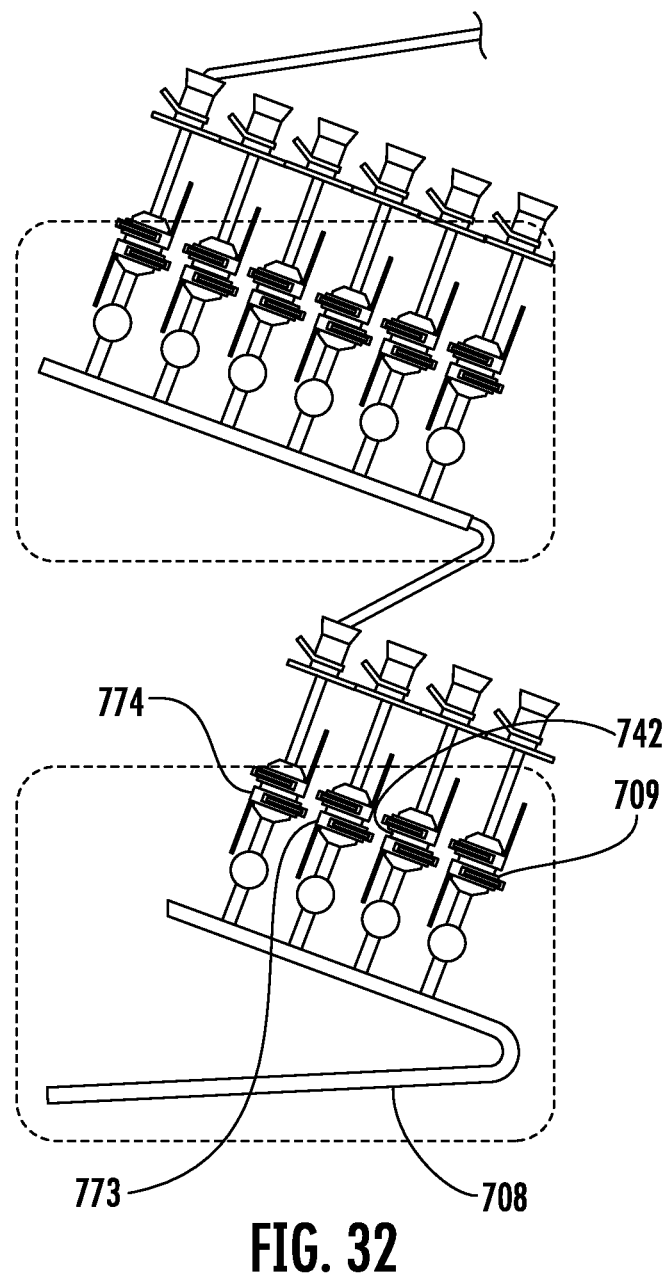
Figure 33:
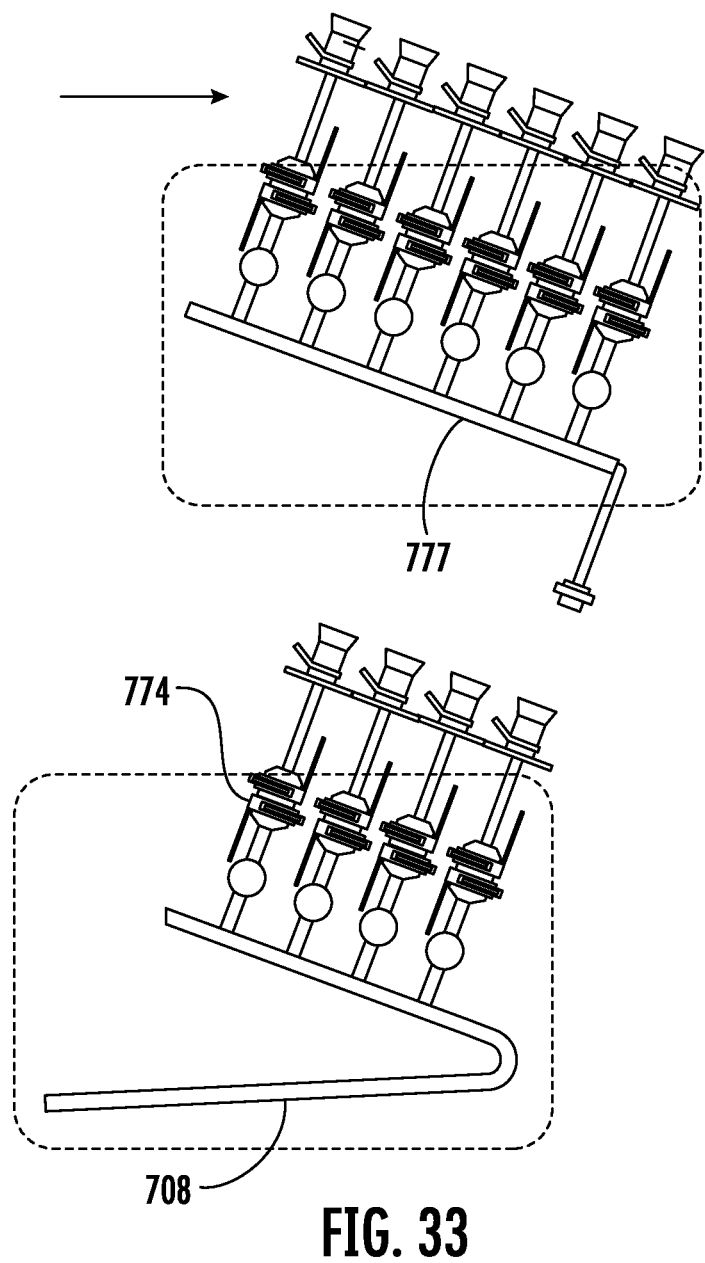

Referring to FIG. 32, the filling sequences depicted in FIGS. 17-31 can be repeated for each one of the remaining outlets 773, 774 of the upstream distributor manifold 708. Referring to FIG. 33, after the fourth intermediary distributor manifold 777 is used to perform filling sequences via the fourth upstream distributor manifold outlet 774 of the first upstream distributor manifold 708, the first upstream distributor manifold 708 can be removed from the distributor skid, and the closed system is opened. After use in the intended bioprocessing application, the first upstream distributor manifold 708 can be disconnected from the distributor skid and replaced with another single use upstream distributor manifold having a similar construction and placed in series connection with one of another set of intermediary distributor manifolds and one of another set of filler manifolds to provide a second closed system.

In embodiments, the fluid distribution system is configured to be used to provide a closed system that can be used for "X" set of filling sequences, wherein the "X" set of filling sequences equals the number of outlets in a first distributor manifold. In embodiments, the fluid distribution system is configured to be used to provide a closed system that can be used for the product of "X" and "Y" sets of filling sequences, wherein the "X" set of filling sequences equals the number of outlets in a first distributor manifold, and the "Y" set of sequences equals the number of outlets in a second distributor manifold connected in series to the first distributor manifold.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The terms "first," "second," etc. are for convenient reference only and are not meant to be limiting, such as with respect to a temporal or a sequential requirement, unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fluid distribution system comprising:
   a first single use distributor manifold, the first single use distributor manifold having a first distributor manifold inlet and a plurality of first distributor manifold outlets in fluid communication with the first distributor manifold inlet;
   a skid, the skid including a pump, the first single use distributor manifold removably mounted to the skid and fluidly arranged with the pump for delivering a supply of fluid to the first distributor manifold inlet;
   a first distributor valve arrangement, the first distributor valve arrangement including a plurality of valves mounted to the skid and arranged with the first single use distributor manifold such that each of the first distributor manifold outlets is independently occludable via a respective one of the valves of the first distributor valve arrangement;
   a set of single use filler manifolds, the set of single use filler manifolds corresponding to the number of first distributor manifold outlets, each single use filler manifold having a filler manifold inlet, a plurality of filler manifold outlets in fluid communication with the filler manifold inlet, and an aseptic fluid connector configured to fluidly connect the filler manifold inlet to one of the plurality of first distributor manifold outlets.

2. The fluid distribution system according to claim 1, further comprising:
   a second single use distributor manifold, the second single use distributor manifold having a second distributor manifold inlet and a plurality of second distributor manifold outlets in fluid communication with the second distributor manifold inlet, the second single use distributor manifold removably mounted to the distributor skid, one of the plurality of second distributor manifold outlets in fluid communication with the first distributor manifold inlet, and the second distributor manifold inlet fluidly arranged with the pump for delivering the supply of fluid to the first distributor manifold inlet through the second single use distributor manifold;
   a second distributor valve arrangement, the second distributor valve arrangement including a plurality of valves mounted to the skid and arranged with the second single use distributor manifold such that each of the second distributor manifold outlets is independently occludable via a respective one of the valves of the second distributor valve arrangement.

3. The fluid distribution system according to claim 2, wherein the first single use distributor manifold is one of a set of first single use distributor manifolds, the set of first single use distributor manifolds corresponding to the number of second distributor manifold outlets, each first single use distributor manifold having an aseptic fluid connector configured to fluidly connect the first single distributor manifold inlet to one of the plurality of second distributor manifold outlets.

4. The fluid distribution system according to claim 1, wherein one of the set of single use filler manifolds is mounted to the skid, the system further comprising:
   a filler valve arrangement, the filler valve arrangement including a plurality of valves mounted to the skid and arranged with the single use filler manifold such that each of the filler manifold outlets is independently occludable via a respective one of the valves of the filler valve arrangement.

5. The fluid distribution system according to claim 4, wherein the valves of the filler valve arrangement are disposed along a vertical axis in spaced relationship to each other.

6. The fluid distribution system according to claim 4, wherein the valves of the filler valve arrangement are disposed along a horizontal axis in spaced relationship to each other.

7. The fluid distribution system according to claim 1, further comprising:
   a distribution tower, wherein one of the set of single use filler manifolds is mounted to the distribution tower;
   a filler valve arrangement, the filler valve arrangement including a plurality of valves mounted to the distribution tower and arranged with the single use filler manifold mounted to the distribution tower such that each of the filler manifold outlets is independently occludable via a respective one of the valves of the filler valve arrangement.

8. The fluid distribution system according to claim 7, wherein the distribution tower comprises a tower and a trolley, the tower extending from the trolley, the one of the set of single use filler manifolds and the filler valve arrangement mounted to the tower.

9. The fluid distribution system according to claim 7, wherein the distribution tower comprises a gantry including first and second uprights and a beam extending between upper ends of the first and second uprights, and the one of the set of single use filler manifolds and the filler valve arrangement mounted to the beam.

10. The fluid distribution system according to claim 1, further comprising:
a plurality of single use containers, each single use container having an access port fluidly connected to a respective one of the filler manifold outlets via an aseptic fluid connector;
a control unit, the control unit including a processor and a non-transitory computer readable medium bearing a fluid distribution program, the processor arranged with the computer readable medium to execute the fluid distribution program, the processor being in electrical communication with the first distributor valve arrangement to selectively operate the valves of the first distributor valve arrangement based upon instructions from the fluid distribution program, the fluid distribution program having a scaling module configured to sequentially open a respective one of the first distributor manifold outlets and close the other of the first distributor manifold outlets to perform a corresponding sequential series of filling operations with a respective one of the set of single use filler manifolds.

11. A method of aseptically distributing fluid, the method comprising:
feeding a fluid into a distributor manifold inlet of a single use distributor manifold;
discharging a first supply of the fluid from a first one of a plurality of distributor manifold outlets of the single use distributor manifold to a filler manifold inlet of a first single use filler manifold via a first aseptic fluid pathway;
discharging portions of the first supply of the fluid respectively from a plurality of filler manifold outlets of the first single use filler manifold to a respective one of a first set of single use containers respectively aseptically fluidly connected to the plurality of filler manifold outlets of the first single use filler manifold;
after discharging the portions of the first supply of the fluid, disconnecting the first single use filler manifold from the single use distributor manifold;
discharging a second supply of the fluid from a second one of the plurality of distributor manifold outlets of the single use distributor manifold to a filler manifold inlet of a second single use filler manifold via a second aseptic fluid pathway;
discharging portions of the second supply of the fluid respectively from a plurality of filler manifold outlets of the second single use filler manifold to a respective one of a second set of single use containers respectively aseptically fluidly connected to the plurality of filler manifold outlets of the second single use filler manifold.

12. The method according to claim 11, further comprising:
sequentially discharging an additional supply of the fluid from each other distributor manifold outlet port of the single use distributor manifold to a filler manifold inlet of a respective other single use filler manifold via a respective separate aseptic fluid pathway;
respectively discharging portions of the additional supply of the fluid from a plurality of filler manifold outlets of each respective other single use filler manifold to a respective one of an additional set of single use containers respectively aseptically fluidly connected to the plurality of filler manifold outlets of each respective other single use filler manifold;
after respectively discharging the portions of the additional supply of the fluid, disconnecting each respective other single use filler manifold from the single use distributor manifold.

13. The method according to claim 12, further comprising:
installing the single use distributor manifold in a filling skid before feeding the fluid into the distributor manifold inlet of the single use distributor manifold;
removing the single use distributor manifold from the filling skid after sequentially discharging the additional supply of the fluid from each other distributor manifold outlet port of the single use distributor manifold.

14. The method according to claim 11, wherein the single use distributor manifold comprises a first single use distributor manifold, and wherein discharging the first supply of the fluid from the first one of a plurality of distributor manifold outlets of the single use distributor manifold includes:
feeding the first supply of the fluid into a distributor manifold inlet of a second single use distributor manifold, the second single use distributor manifold in the first aseptic fluid pathway interposed between the first one of the plurality of distributor manifold outlets of the first single use distributor manifold and the filler manifold inlet of the first single use filler manifold, and
discharging the first supply of the fluid from a first one of a plurality of distributor manifold outlets of the second single use distributor manifold to the filler manifold inlet of the first single use filler manifold via the first aseptic fluid pathway.

15. A method of aseptically distributing fluid, the method comprising:
feeding a first supply of fluid into a distributor manifold inlet of a first single use distributor manifold;
discharging a first supply of fluid from a first one of a plurality of distributor manifold outlets of the first single use distributor manifold to a distributor manifold inlet of a second single use distributor manifold via a first aseptic fluid pathway;
discharging the first supply of fluid from a first one of a plurality of distributor manifold outlets of the second single use distributor manifold to a filler manifold inlet of a first single use filler manifold via a second aseptic fluid pathway;
discharging portions of the first supply of fluid respectively from a plurality of filler manifold outlets of the first single use filler manifold to a respective one of a first set of single use containers respectively aseptically fluidly connected to the plurality of filler manifold outlets of the first single use filler manifold;
after discharging the portions of the first supply of fluid, disconnecting the first single use filler manifold from the second single use distributor manifold and connecting a second single use filler manifold to a second one of the plurality of distributor manifold outlets of the second single use distributor manifold via a third aseptic fluid pathway;
feeding a second supply of fluid into the distributor manifold inlet of the first single use distributor manifold;
discharging the second supply of fluid from the first one of the plurality of distributor manifold outlets of the first single use distributor manifold to the distributor manifold inlet of the second single use distributor manifold via the first aseptic fluid pathway;

discharging the second supply of fluid from a second one of the plurality of distributor manifold outlets of the second single use distributor manifold to a filler manifold inlet of the second single use filler manifold via the third aseptic fluid pathway;

discharging portions of the second supply of fluid respectively from a plurality of filler manifold outlets of the second single use filler manifold to a respective one of a second set of single use containers respectively aseptically fluidly connected to the plurality of filler manifold outlets of the second single use filler manifold.

16. The method according to claim 15, further comprising:

sequentially discharging an additional supply of fluid from each other distributor manifold outlet port of the second single use distributor manifold to a filler manifold inlet of a respective other single use filler manifold via a respective separate aseptic fluid pathway;

respectively discharging portions of the additional supply of fluid from a plurality of filler manifold outlets of each respective other single use filler manifold to a respective one of an additional set of single use containers respectively aseptically fluidly connected to the plurality of filler manifold outlets of each respective other single use filler manifold.

17. The method according to claim 16, further comprising:

after respectively discharging the portions of the additional supply of fluid, disconnecting each respective other single use filler manifold from the second single use distributor manifold;

after sequentially discharging the additional supply of fluid from each other distributor manifold outlet port of the second single use distributor manifold, disconnecting the second single use distributor manifold and connecting a second one of the plurality of distributor manifold outlets of the first single use distributor manifold to a distributor manifold inlet of a third single use distributor manifold via a fourth aseptic fluid pathway.

18. The method according to claim 17, further comprising:

feeding a third supply of fluid into the distributor manifold inlet of the first single use distributor manifold;

discharging the third supply of fluid from the second one of the plurality of distributor manifold outlets of the first single use distributor manifold to the distributor manifold inlet of the third single use distributor manifold via the fourth aseptic fluid pathway;

discharging the third supply of fluid from a first one of a plurality of distributor manifold outlets of the third single use distributor manifold to a filler manifold inlet of a third single use filler manifold via a fifth aseptic fluid pathway;

discharging portions of the third supply of fluid respectively from a plurality of filler manifold outlets of the third single use filler manifold to a respective one of a third set of single use containers respectively aseptically fluidly connected to the plurality of filler manifold outlets of the third single use filler manifold.

19. The method according to claim 18, further comprising:

sequentially discharging an additional supply of fluid from each other distributor manifold outlet port of the third single use distributor manifold to a filler manifold inlet of a respective other single use filler manifold via a respective separate aseptic fluid pathway;

respectively discharging portions of the additional supply of fluid from a plurality of filler manifold outlets of each respective other single use filler manifold to a respective one of an additional set of single use containers respectively aseptically fluidly connected to the plurality of filler manifold outlets of each respective other single use filler manifold.

20. The method according to claim 19, further comprising:

sequentially discharging a respective one of an additional set of supplies of fluid from each other distributor manifold outlet port of the first single use distributor manifold to a set of intermediary single use distributor manifolds.

* * * * *

(12) EX PARTE REEXAMINATION CERTIFICATE (13060th)

United States Patent
Seal et al.

(10) Number: US 11,814,200 C1
(45) Certificate Issued: Oct. 16, 2025

(54) FLUID DISTRIBUTION SYSTEM WITH SINGLE USE MANIFOLD ASSEMBLY FOR SCALED FILLING

(71) Applicant: Cytiva US LLC, Marlborough, MA (US)

(72) Inventors: Michael B. Seal, Hampshire (GB); Bojan Isailovic, Hampshire (GB); Robert Flisar, Dreieich (DE); Jeremy Rautenbach, Cheltenham (AU)

(73) Assignee: PALL CORPORATION, Port Washington, NY (US)

Reexamination Request:
No. 90/019,587, Jul. 18, 2024

Reexamination Certificate for:
Patent No.: 11,814,200
Issued: Nov. 14, 2023
Appl. No.: 17/934,962
Filed: Sep. 23, 2022

Related U.S. Application Data

(60) Provisional application No. 63/295,483, filed on Dec. 30, 2021.

(51) Int. Cl.
*B65B 3/00* (2006.01)
*B65B 3/12* (2006.01)
*B65B 3/34* (2006.01)
*B65B 55/24* (2006.01)
*B67C 3/22* (2006.01)
*B67C 3/28* (2006.01)

(52) U.S. Cl.
CPC ............... *B65B 3/003* (2013.01); *B65B 3/12* (2013.01); *B65B 3/34* (2013.01); *B65B 55/24* (2013.01); *B67C 3/225* (2013.01); *B67C 3/282* (2013.01); *B67C 2003/228* (2013.01)

(58) Field of Classification Search
None
See application file for complete search history.

(56) References Cited

To view the complete listing of prior art documents cited during the proceeding for Reexamination Control Number 90/019,587, please refer to the USPTO's Patent Electronic System.

*Primary Examiner* — Terrence R Till

(57) ABSTRACT

A fluid distribution system includes single use distributor manifolds each having a distributor manifold inlet and a plurality of distributor manifold outlets in fluid communication with the distributor manifold inlet. A set of single use filler manifolds can be sequentially connected to a respective one of the outlets of a single use distributor manifold immediately upstream of the connection point of the set of single use filler manifolds. In embodiments, an upstream distributor manifold can be used to feed fluid to a set of intermediary distributor manifolds where the set of intermediary distributor manifolds corresponds to the number of outlets of the upstream distributor manifold.

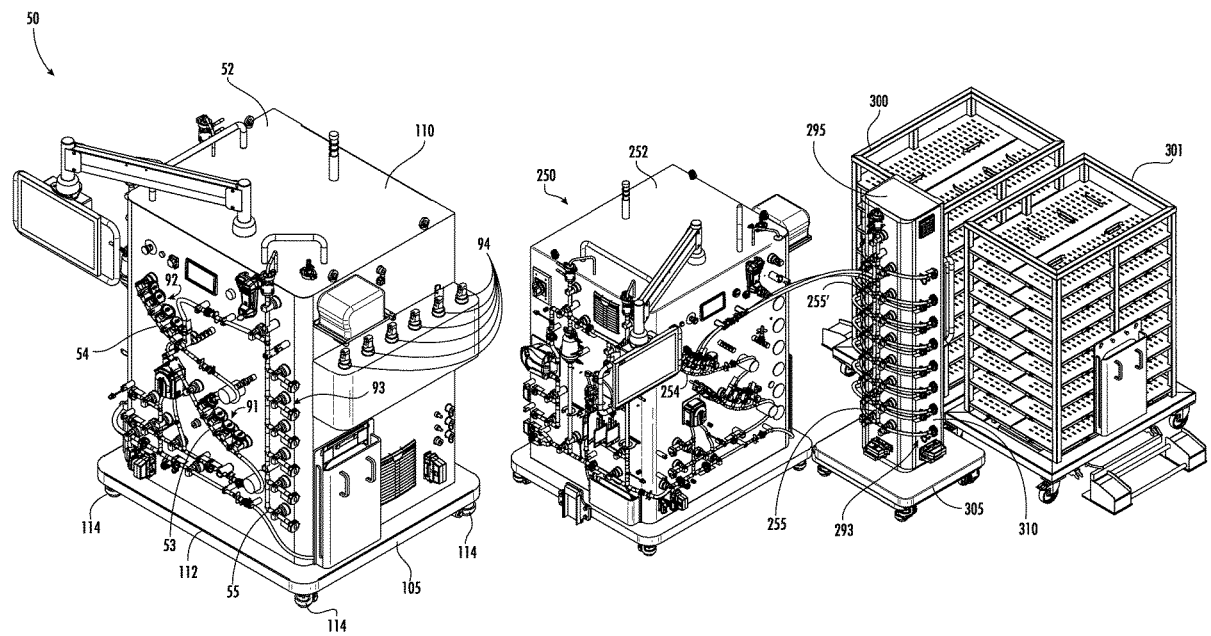

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15-20 is confirmed.

Claims 1, 10, 11 and 13 are determined to be patentable as amended.

Claims 2-9, 12 and 14, dependent on an amended claim, are determined to be patentable.

1. A fluid distribution system comprising:
   a first single use distributor manifold, the first single use distributor manifold having a first distributor manifold inlet and a plurality of first distributor manifold outlets in fluid communication with the first distributor manifold inlet;
   a skid, the skid including a pump, the first single use distributor manifold removably mounted to the skid and fluidly arranged with the pump for delivering a supply of fluid to the first distributor manifold inlet;
   a first distributor valve arrangement, the first distributor valve arrangement including a plurality of valves mounted to the skid and arranged with the first single use distributor manifold such that each of the first distributor manifold outlets is independently occludable via a respective one of the valves of the first distributor valve arrangement;
   a set of single use filler manifolds, the set of single use filler manifolds corresponding to the number of first distributor manifold outlets, each single use filler manifold having a filler manifold inlet, a plurality of filler manifold outlets in fluid communication with the filler manifold inlet, and an aseptic fluid connector configured to fluidly connect the filler manifold inlet to one of the plurality of first distributor manifold outlets*;*
   *a control unit, the control unit including a processor and a non-transitory computer readable medium bearing a fluid distribution program, the processor arranged with the computer readable medium to execute the fluid distribution program, the processor being in electrical communication with the first distributor valve arrangement to selectively operate the valves of the first distributor valve arrangement based upon instructions from the fluid distribution program, the fluid distribution program having a scaling module configured to sequentially open a respective one of the first distributor manifold outlets and occlude the other of the first distributor manifold outlets to perform a corresponding sequential series of filling operations with a respective one of the set of single use filler manifolds.*

10. The fluid distribution system according to claim 1, further comprising:
    a plurality of single use containers, each single use container having an access port fluidly connected to a respective one of the filler manifold outlets via an aseptic fluid connector [*;*
    a control unit, the control unit including a processor and a non-transitory computer readable medium bearing a fluid distribution program, the processor arranged with the computer readable medium to execute the fluid distribution program, the processor being in electrical communication with the first distributor valve arrangement to selectively operate the valves of the first distributor valve arrangement based upon instructions from the fluid distribution program, the fluid distribution program having a scaling module configured to sequentially open a respective one of the first distributor manifold outlets and close the other of the first distributor manifold outlets to perform a corresponding sequential series of filling operations with a respective one of the set of single use filler manifolds].

11. A method of aseptically distributing fluid, the method comprising:
    feeding a fluid into a distributor manifold inlet of a single use distributor manifold *by operating a pump mounted to a filling skid and arranged upstream of the single use distributor manifold*;
    discharging a first supply of the fluid from a first one of a plurality of distributor manifold outlets of the single use distributor manifold to a filler manifold inlet of a first single use filler manifold via a first aseptic fluid pathway;
    discharging, *by operating the pump,* portions of the first supply of the fluid respectively from a plurality of filler manifold outlets of the first single use filler manifold to a respective one of a first set of single use containers respectively aseptically fluidly connected to the plurality of filler manifold outlets of the first single use filler manifold;
    after discharging the portions of the first supply of the fluid, disconnecting the first single use filler manifold from the single use distributor manifold;
    discharging a second supply of the fluid from a second one of the plurality of distributor manifold outlets of the single use distributor manifold to a filler manifold inlet of a second single use filler manifold via a second aseptic fluid pathway;
    discharging, *by operating the pump,* portions of the second supply of the fluid respectively from a plurality of filler manifold outlets of the second single use filler manifold to a respective one of a second set of single use containers respectively aseptically fluidly connected to the plurality of filler manifold outlets of the second single use filler manifold.

13. The method according to claim 12, further comprising:
    installing the single use distributor manifold in [a] *the* filling skid before feeding the fluid into the distributor manifold inlet of the single use distributor manifold;
    removing the single use distributor manifold from the filling skid after sequentially discharging the additional supply of the fluid from each other distributor manifold outlet port of the single use distributor manifold.

* * * * *